United States Patent [19]

Yamada et al.

[11] Patent Number: 5,589,478
[45] Date of Patent: Dec. 31, 1996

[54] BENZENESULFONAMIDE DERIVATIVE AND PROCESS FOR PREPARING THEREOF

[75] Inventors: Koichiro Yamada; Kōsuke Yasuda, both of Saitama-ken; Kohei Kikkawa, Kawaguchi; Rikako Kohno, Omiya, all of Japan

[73] Assignee: Tanabe Seiyaku Co., Ltd., Osaka, Japan

[21] Appl. No.: 356,958

[22] Filed: Dec. 16, 1994

[30] Foreign Application Priority Data

Dec. 17, 1993 [JP] Japan .................... 5-318779
Jun. 23, 1994 [JP] Japan .................... 6-140628
Aug. 4, 1994 [JP] Japan .................... 6-183553

[51] Int. Cl.$^6$ .............. C07D 239/32; C07D 239/42; A61K 31/50; A61K 31/505
[52] U.S. Cl. .............. 514/269; 544/295; 544/296; 544/319; 544/238; 544/123; 544/321; 544/318; 514/272; 514/273; 514/274
[58] Field of Search .............. 544/295, 296, 544/319, 238, 123, 321, 318; 514/269, 272, 273, 274

[56] References Cited

U.S. PATENT DOCUMENTS 3,317,536  5/1967  Grussner et al. .............. 544/318
5,270,313  12/1993  Burri et al. .............. 514/252
5,292,740  3/1994  Burri et al. .............. 514/256

FOREIGN PATENT DOCUMENTS 0569193  11/1993  European Pat. Off. .
6-211810  2/1994  Japan .............. C07D 239/47

OTHER PUBLICATIONS

Chemical Abstracts, vol. 121, No. 230786g (1994).

*Primary Examiner*—Matthew V. Grumbling
*Attorney, Agent, or Firm*—Finnegan, Henderson, Farabow, Garrett & Dunner, L.L.P.

[57] ABSTRACT

A benzenesulfonamide derivative of the formula [I]:

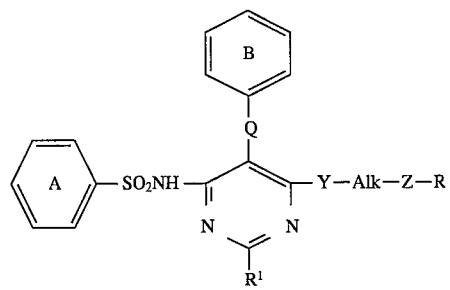

wherein Ring A and Ring B are the same or different and each substituted or unsubstituted benzene ring, Q is a single bond or a group of the formula: —O—, —S—, —SO—, —SO$_2$— or —CH2—, Y is a group of the formula: —O—, —S— or —NH—, Alk is lower alkylene group or lower alkenylene group, Z is a single bond or a group of the formula: —O— or —NH—, R is a substituted or unsubstituted aromatic heterocyclic or aryl group, R$^1$ is hydrogen atom, trifluoromethyl group, substituted or unsubstituted lower alkyl group, substituted or unsubstituted lower alkenyl group, mono— or di-lower alkylamino group, substituted or unsubstituted lower alkylthio group, substituted or unsubstituted lower alkoxy group, substituted or unsubstituted lower alkynyl group, aromatic heterocyclic group, substituted or unsubstituted aliphatic heterocyclic group or aryl group, provided that when Z is a single bond, R is a substituted or unsubstituted aromatic heterocyclic group, or a pharmaceutically acceptable salt thereof, and processes for preparing the same, these compounds having endothelin antagonistic activity and being useful in the prophylaxis or treatment of various diseases caused by endothelin.

15 Claims, No Drawings

BENZENESULFONAMIDE DERIVATIVE AND PROCESS FOR PREPARING THEREOF

FIELD OF THE INVENTION

The present invention relates to a novel benzenesulfonamide derivative having endothelin antagonistic activity, and a process for preparing the same.

PRIOR ART

Endothelin is a polypeptide consisting of 21 amino acids which is first isolated from the culture supernatant of porcine aortic endothelial cells. Now, it is known to be a potent vasoconstrictor, bronchoconstrictor and mitogen. It has also been reported that the level of endothelin is significantly increased in the blood of patients with essential hypertension, acute myocardial infarction, pulmonary hypertension, Raynaud disease, diabetes, atherosclerosis, and in the blood and the washing of airway of patients with asthma, compared with that of the normal human being. Thus, endothelin is an endogenous bioactive substance which stimulates durably and directly or indirectly the vascular or non-vascular smooth muscle. The excess production or excess secretion of endothelin seems to be one of the causes for hypertension, pulmonary hypertension, renal hypertension, Raynaud disease, bronchial asthma, gastric ulcer, inflammatory bowl disease (Crohn's disease), shock, carcinogenesis, restenosis after angioplasty, organ dysfunction after transplantation, diabetes, thrombosis, arteriosclerosis, heart failure, acute renal insufficiency, glomerulonephritis, cyclosporin-induced nephrotoxicity, myocardial infarction, angina pectoris, arrhythmia, glaucoma, migraine, cerebrovascular spasm and cerebral infarction. Thus, a compound which strongly antagonizes endothelin has been considered to be useful in the treatment of the above various diseases.

On the other hand, Japanese Patent First Publication (Kokai) Nos. 155864/1993 and 222003/1993 disclose as a benzenesulfonamide derivative having endothelin antagonistic activity N-{[5-substituted phenyl (or substituted phenoxy)]-6-hydroxyalkoxypyrimidin-4-yl}-substituted benzenesulfonamides, and the like.

BRIEF DESCRIPTION OF THE INVENTION

An object of the present invention is to provide a novel benzenesulfonamide derivative having an excellent endothelin antagonistic activity. Another object of the present invention is to provide processes for preparing the same.

DETAILED DESCRIPTION OF THE INVENTION

The present invention relates to a benzenesulfonamide derivative of the formula [I]:

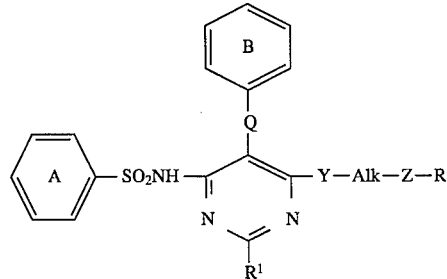

wherein Ring A and Ring B are the same or different and each a substituted or unsubstituted benzene ring, Q is a single bond or a group of the formula: —O—, —S—, —SO—, —SO$_2$— or —CH$_2$—, Y is a group of the formula: —O—, —S— or —NH—, Alk is a lower alkylene group or a lower alkenylene group, Z is a single bond or a group of the formula: —O— or —NH—, R is a substituted or unsubstituted aromatic heterocyclic or aryl group, R$^1$ is hydrogen atom, trifluoromethyl group, a substituted or unsubstituted lower alkyl group, a substituted or unsubstituted lower alkenyl group, a mono— or di-lower alkylamino group, a substituted or unsubstituted lower alkylthio group, a substituted or unsubstituted lower alkoxy group, a substituted or unsubstituted lower alkynyl group, an aromatic heterocyclic group, a substituted or unsubstituted aliphatic heterocyclic group or an aryl group, provided that when Z is a single bond, R is a substituted or unsubstituted aromatic heterocyclic group, or a pharmaceutically acceptable salt thereof.

In the present compounds [I], the substituent of Ring A or Ring B includes, for example, a halogen atom; a lower alkyl group; a lower alkoxy group; a lower alkenyl group; a lower alkynyl group; a cycloalkyl group; a lower alkylthio group; trifluoromethyl group; carboxyl group; cyano group; tetrazolyl group; formyl group; carbamoyl group; a mono- or di-lower alkylaminocarbonyl group; a lower alkoxycarbonyl group; a lower alkoxycarbonyl-lower alkoxy group; a lower alkoxycarbonyl-lower alkyl group; a lower alkoxycarbonyl-lower alkenyl group; a di-lower alkoxy-substituted lower alkyl group; a hydroxy-substituted lower alkyl group; a carboxyl-substituted lower alkyl group; a carboxyl-substituted lower alkenyl group; a carboxy-substituted lower alkoxy group; a bromopyrimidinyloxy-lower alkyl group; a lower alkylenedioxy group; an aryl-lower alkoxy group; or an arylaminocarbonyl group, and the like.

The substituent of the lower alkyl group includes, for example, a halogen atom, carboxyl group, a lower alkoxycarbonyl group, an aromatic heterocyclic group or an aryl group, and the like. The substituent of the lower alkoxy group includes, for example, hydroxy group, a hydroxy-lower alkoxy group, and the like. The substituent of the lower alkynyl group includes, for example, carboxyl group, and the like. The substituent of the aliphatic heterocyclic group includes, for example, a lower alkyl group, and the like.

The substituent of the aromatic heterocyclic or aryl group includes, for example, a halogen atom; a protected or unprotected hydroxy group; nitro group; cyano group; amino group; formyl group; carboxyl group; carbamoyl group; an N-lower alkylcarbamoyloxy group; an N-hydroxyiminomethyl group; an N-lower alkoxyiminomethyl group; a lower alkyl group; a hydroxy-substituted lower alkyl group; a cycloalkyl group; a lower alkoxy-lower alkyl group; a lower alkoxycarbonyl-lower alkenyl group; trifluoromethyl group; a hydroxy- and aryl-substituted lower alkyl group; a lower alkylthio group; a mono- or di-lower alkylamino group; a lower alkanoylamino group; a lower alkoxy group; a lower alkoxy group substituted by a protected or unprotected carboxyl group; an aryloxy group; a lower alkoxycarbonyl group; a lower alkoxy-lower alkenyl group; a lower alkanoyl group; an arylcarbonyl group; a lower alkenyloxy group; a hydroxy-substituted lower alkynyl group; a lower alkynyl group being optionally protected by a trimethylsilyl group; a cyano-lower alkoxy group; a cycloalkyl-lower alkoxy group; a lower alkylsulfinyl group; a lower alkylsulfonyl group; an aryl group; a phenyl-lower alkyl group; an aromatic heterocyclic-substituted lower alkyl group; an aromatic heterocyclic-substituted lower alkoxy group; a phenyl-lower alkenyl group; a phenyl-lower alkoxy group; an arylcarbonylamino group; an aromatic heterocyclic-substituted oxy group having optionally 1 to 3 substituents selected from a halogen atom and a lower alkyl group; or an aromatic heterocyclic group having optionally a lower alkyl substituent, and the like.

Ring A and/or Ring B may have the same or different 1 to 3 substituents of the above mentioned substituents. The lower alkyl group, the aromatic heterocyclic group and/or the aryl group may have the same or different 1 to 4 substituents of the above mentioned substituents, respectively.

The protecting group for hydroxy group and/or carboxyl group may be any conventional one which can be a protecting group for hydroxy group and/or carboxyl group, respectively, and the protecting group for hydroxy group includes, for example, benzyl group, methoxymethyl group, tetrahydropyranyl group, and the like, and the protecting group for carboxyl group includes, for example, methyl group, ethyl group, tert-butyl group, benzyl group, and the like.

The aromatic heterocyclic group is preferably an aromatic heteromonocyclic or heterobicyclic group having 1 to 4 heteroatoms selected from nitrogen atom, oxygen atom and sulfur atom, for example, pyrrolyl group, imidazolyl group, furyl group, thienyl group, thiazolyl group, isooxazolyl group. oxazolyl group, oxazolinyl group, pyrazolyl group, quinazolinyl group, thienopyrimidinyl group, pyridyl group, pyrimidinyl group, pyridazinyl group, pyrazinyl group, triazinyl group, tetrazolyl group, quinolyl group, isoquinolyl group, quinoxalinyl group, benzothiazolyl group, benzoxazolyl group, benzimidazolyl group, and the like.

The aryl group and the aryl moiety in the arylcarbonylamino group, the arylaminocarbonyl group, the aryloxy group and the arylcarbonyl group are, for example, phenyl group, a lower alkoxyphenyl group or naphthyl group.

The aliphatic heterocyclic group is preferably an aliphatic heteromonocyclic or heterobicyclic group having 1 to 4 heteroatoms selected from nitrogen atom, oxygen atom and sulfur atom, for example, piperazinyl group, pyrrolidinyl group, piperidyl group, homopiperidyl group, thiomorpholinyl group, morpholinyl group, and the like.

Among the desired compounds [I] of the present invention, the pharmaceutically preferable compounds are compounds of the formula [I] wherein Ring A is a benzene ring substituted by a lower alkyl group; one or two lower alkoxy groups; a lower alkoxycarbonyl-lower alkyl group; a hydroxy-substituted lower alkyl group; or a lower alkoxycarbonyl-lower alkoxy group, Ring B is a benzene ring substituted by formyl group; trifluoromethyl group; a lower alkyl group; one or two lower alkoxy groups; a lower alkylenedioxy group; a hydroxy-lower alkyl group; or a lower alkoxycarbonyl group, Q is a single bond or a group of the formula: —O— or —S—, Y is a group of the formula: —O—, Alk is a lower alkylene group, Z is a group of the formula: —O—, R is a phenyl group having optionally a substituent selected from amino group, nitro group, a halogen atom and a hydroxy-lower alkyl group; a pyridyl group having optionally a substituent selected from amino group, nitro group, trifluoromethyl group and a lower alkanoylamino group; a pyrimidinyl group having optionally a substituent selected from a halogen atom, formyl group, thienyl group, furyl group, pyridyl group, a lower alkyl group, a lower alkylthio group, a lower alkanoyl group, a lower alkynyl group, a lower alkenyloxy group, a lower alkoxy group, a lower alkylsulfinyl group, a lower alkylsulfonyl group, a cyano-substituted lower alkoxy group, thiazolyl group, a lower alkyl-substituted thienyl group, a lower alkyl-substituted pyrrolyl group, a phenyl group and a lower alkoxyphenyl group; or a benzothiazolyl group, and $R^1$ is hydrogen atom, a lower alkyl group, pyridyl group, morpholinyl group or pyrimidinyl group.

The pharmaceutically more preferable compounds are compounds of the formula [I] wherein Ring A is a benzene ring substituted by a lower alkyl group, Ring B is a benzene ring substituted by a halogen atom, a lower alkyl group or a lower alkoxy group, R is a pyrimidinyl group substituted by a halogen atom, thienyl group, furyl group or a lower alkylthio group, and $R^1$ is hydrogen atom or pyrimidinyl group.

Among the desired compounds [I] of the present invention, other preferable compounds are compounds of the formula [I] wherein Ring A is a benzene ring substituted by a lower alkyl group, Ring B is a benzene ring substituted by a lower alkyl group or a lower alkoxy group, Q is a single bond or a group of the formula: —O—, Y is a group of the formula: —O—, Alk is a lower alkylene group, Z is a group of the formula: —O—, R is a pyrimidinyl group having optionally a substituent selected from a halogen atom, formyl group, cyano group, hydroxy group, a lower alkoxy group, a lower alkylthio group, a lower alkanoyl group, a lower alkenyloxy group, a lower alkynyl group, a lower alkylsulfonyl group, a lower alkylsufinyl group, a lower alkylamino-lower alkanoyloxy group, a cyano-lower alkoxy group, a hydroxy-lower alkyl group, a lower alkoxyolower alkenyl group, a lower alkyl-pyrrolyl group, thiazolyl group, thienyl group, a lower alkyl-thienyl group, furyl group, pyridyl group, a di-lower alkyl-oxazolinyl group and phenyl group, and $R^1$ is hydrogen atom, pyridyl group, pyrimidinyl group or morpholinyl group.

The more preferable compounds are compounds of the formula [I] wherein R is a pyrimidinyl group having a substituent selected from a halogen atom, a lower alkylthio group, a lower alkoxy group, a lower alkanoyl group, a hydroxy-lower alkyl group, a lower alkoxy-lower alkenyl group, thienyl group, furyl group, pyridyl group and phenyl group, and $R^1$ is hydrogen atom, pyrimidinyl group or morpholinyl group.

The desired compounds [I] of the present invention may exist in the form of an optical isomer based on an asymmetric carbon atom thereof, and the present invention also includes these optical isomers and a mixture thereof.

The desired compounds [I] of the present invention may be clinically used either in the form of a free form or in the form of a pharmaceutically acceptable salt thereof. The pharmaceutically acceptable salt includes an acid-addition salt with an inorganic acid or organic acid, salts with an inorganic base, organic base or amino acid, for example, hydrochloride, sulfate, hydrobromide, methanesulfonate, acetate, fumarate, maleate, oxalate, an alkali metal salt (e.g. sodium, potassium, etc.), an alkaline earth metal salt (e.g. magnesium, calcium, etc.), triethylamine salt, a salt with lysine, and the like.

The desired compounds [I] of the present invention or a pharmaceutically acceptable salt thereof may be administered either orally or parenterally in the form of a conventional pharmaceutical preparation such as tablets, granules, capsules, powders, injections, inhalants, and the like.

The dosage of the desired compounds [I] of the present invention and a pharmaceutically acceptable salt thereof may vary according to the administration route, ages, weights and conditions of the patients, but it is usually in the range of about 0.01 to 100 mg/kg/a day.

According to the present invention, the desired compounds [I] may be prepared by the following Process A, B, C or D.

Process A

The desired compounds [I] of the present invention may be prepared by reacting a compound of the formula [II]:

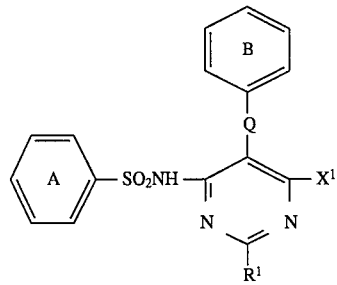
[II]

wherein $X^1$ is a reactive residue, and the other symbols are the same as defined above, with a compound of the formula [III]:

H-Y-Alk-Z-R  [III]

wherein the symbols are the same as defined above, or a salt thereof.

Process B

The compounds [I] may also be prepared by reacting a compound of the formula [IV]:

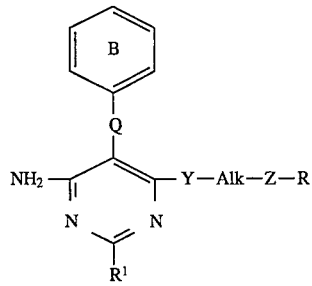
[IV]

wherein the symbols are the same as defined above, or a salt thereof, with a compound of the formula [V]:

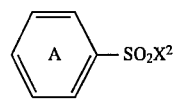
[V]

wherein $X^2$ is a reactive residue, and Ring A is the same as defined above.

Process C

Among the desired compounds [I] of the present invention, the compound of the formula [I] wherein Z is a group of the formula: —O— or —NH—, i.e. the compound of the formula [I-a]:

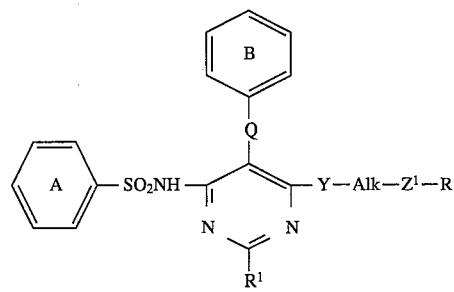
[I-a]

wherein $Z^1$ is a group of the formula: —O— or —NH—, and the other symbols are the same as defined above, may be prepared by reacting a compound of the formula [VI]:

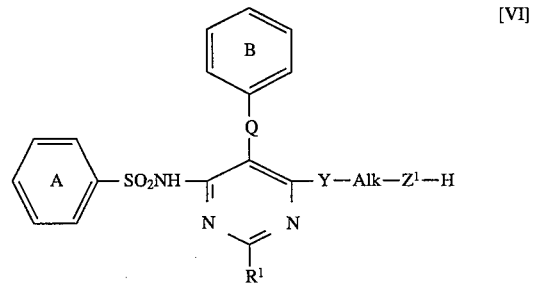
[VI]

wherein the symbols are the same as defined above, or a salt thereof, with a compound of the formula [VII]:

$X^3$—R  [VI]

wherein $X^3$ is a reactive residue, and the other symbols are the same as defined above.

Process D

Moreover, among the desired compounds [I] of the present invention, the compound of the formula [I] wherein Q is a single bond, i.e. the compound of the formula [I-b]:

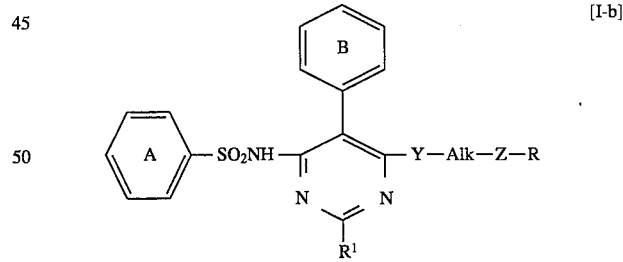
[I-b]

wherein the symbols are the same as defined above, may be prepared by reacting a compound of the formula [VIII]:

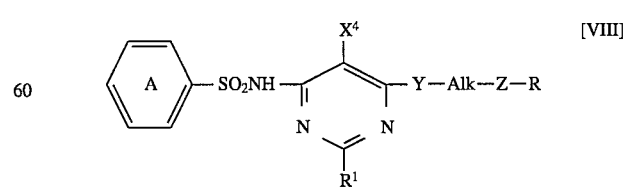
[VIII]

wherein $X^4$ is a reactive residue, and the other symbols are the same as defined above, or a salt thereof, with a compound of the formula [IX]:

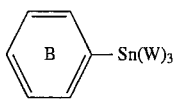

[IX]

wherein W is a lower alkyl group, and Ring B is the same as defined above.

The salts of the compounds [III], [IV], [VI] and [VIII] are, for example, salts with an inorganic acid (e.g. hydrochloride, sulfate, etc.), and salts with an inorganic base (e.g. an alkali metal salt, an alkaline earth metal salt, etc.).

The reactive residues for $X^1$, $X^2$, $X^3$ and $X^4$ are preferably a halogen atom, a lower alkylsulfonyloxy group or an arylsulfonyloxy group, but a halogen atom is more preferable.

The above Processes are preferably carried out as follows.

Process A

The reaction of the compound [II] and the compound [III] or a salt thereof is carried out in the presence of an acid acceptor in a suitable solvent or without a solvent. The acid acceptor is preferably an alkali metal hydride, an alkali metal carbonate, an alkali metal amide, an alkali metal alkoxide, an alkylalkali metal, an alkali metal, an alkaline earth metal, an alkali metal hydroxide, an alkaline earth metal hydroxide, an organic base (e.g. 1,8-diazabicyclo [5.4.0]-undeca-7-ene, etc.), and the like. The solvent includes, for example, dimethylsulfoxide, dimethylacetamide, dimethylformamide, hexamethylphosphoramide, sulfolane, 1,3-dimethyl-2-imidazolidinone, dioxane, tetrahydrofuran, toluene, ethylene glycol dimethyl ether, and the like. The reaction is preferably carried out at a temperature from room temperature to 150° C., preferably at a temperature from room temperature to 100° C.

Process B

The reaction of the compound [IV] or a salt and the compound [V] is carried out in the presence of an acid acceptor in a suitable solvent or without a solvent. The acid acceptor and the solvent may be the same acid acceptors or the solvents for the above Process A. The reaction is preferably carried out at a temperature from 0° C. to 150° C., more preferably at a temperature from room temperature to 100° C. The reaction may preferably proceed in the presence of a catalytic amount of a phase transfer catalyst such as tetrabutylammonium hydrogen sulfate, trimethylbenzylammonium chloride, 18-crown-6, etc.

Process C

The reaction of the compound [VI] or a salt thereof and the compound [VIII] is carried out in the presence of an acid acceptor in a suitable solvent or without a solvent. The acid acceptor may be the same acid acceptor for the above mentioned Process A. The solvent includes, for example, dimethylsulfoxide, dimethylacetamide, dimethylformamide, 1,3-dimethyl-2-imidazolidinone, ethylene glycol dimethyl ether, hexamethylphosphoramide, sulfolane, dioxane, tetrahydrofuran, toluene, and the like. The reaction is preferably carried out at a temperature from room temperature to 150° C., more preferably at a temperature from room temperature to 100° C.

Process D

The reaction of the compound [VIII] or a salt thereof and the compound [IX] is carried out in the presence of a catalyst in a suitable solvent. The catalyst includes, for example, a palladium catalyst such as bis(triphenylphosphine)palladium (II) chloride, palladium (II) acetate, tetrakis(triphenylphosphine)palladium (0), and the like. The reaction may preferably proceed in the presence of a copper (I) salt such as copper (I) chloride, copper (I) bromide, copper (I) iodide, etc., according to the method disclosed in Journal of Organic Chemistry Vol. 58, p. 1963 (1993). The solvent includes, for example, dioxane, ethylene glycol dimethyl ether, dimethylacetamide, dimethylformamide, hexamethylphosphoramide, benzene, tetrahydrofuran, toluene, ethyl acetate, a lower alcohol, methylene chloride, chloroform, carbon tetrachloride, 1,3-dimethyl-2-imidazolidinone, acetic acid, diethyl ether, dimethoxyethane, water, or a mixture thereof. The reaction is preferably carried out at a temperature from 50° C. to 100° C.

The desired compounds [I] of the present invention can be converted each other to the other desired compound [I]. Such conversion of the present compounds [I] into the other compound [I] may be carried out according to the kinds of the substituents thereof, but is carried out according to the following Step (a) to (w).

Step (a)

The desired compound [I] wherein R is a substituted aromatic heterocyclic or aryl group can be prepared by reacting the compound [I] wherein the corresponding R is a halogen-substituted aromatic heterocyclic or aryl group with a trialkyl-tin compound with the group to substitute in the presence of a catalyst. The catalyst may be any ones which are used in the above mentioned Process D. The reaction is preferably carried out at a temperature from room temperature to 100° C.

Step (b)

The desired compound [I] wherein R is a lower alkanoyl group (e.g. acetyl group, etc.)-substituted aromatic heterocyclic or aryl group can be prepared by acid-treatment of the compound [I] wherein the corresponding R is a lower alkoxy-lower alkenyl group (e.g. 1-ethoxyvinyl group, etc.)-substituted aromatic heterocyclic or aryl group. The acid includes, for example, hydrochloric acid, sulfuric acid, p-toluenesulfonic acid, methanesulfonic acid, trifluoroacetic acid, acetic acid, etc. The reaction is preferably carried out at a temperature from 0° C. to room temperature.

Step (c)

The desired compound [I] wherein R is a hydroxy-substituted lower alkyl group-substituted aromatic heterocyclic or aryl group can be prepared by treating the compound [I] wherein the corresponding R is a lower alkanoyl- or formyl-substituted aromatic heterocyclic or aryl group with a reducing agent. The reducing agent includes, for example, sodium borohydride, lithium borohydride, lithium aluminum hydride, di-isobutyl aluminum hydride, etc. The reaction is preferably carried out at a temperature from 0° C. to room temperature.

Step (d)

The desired compound [I] wherein R is a lower alkyl group-substituted aromatic heterocyclic or aryl group can be prepared by subjecting the compound [I] wherein the corresponding R is a hydroxy-substituted lower alkyl-substituted aromatic heterocyclic or aryl group to halogenation, followed by reduction of the product. The halogenation reaction is carried out by reacting the compound [I] with a halogenating agent such as thionyl chloride, phosphorus oxychloride, phosphorus pentachloride, phosphorus tribromide, etc. The reduction is carried out by treating with a palladium catalyst such as palladium-carbon, palladium-barium sulfate, palladium-aluminum oxide, palladium-black, etc., preferably in the presence of an acid acceptor under hydrogen atmosphere. The acid acceptor is preferably triethylamine, pyridine, potassium carbonate, sodium hydrogen carbonate, sodium acetate, etc. The reaction is preferably carried out at a temperature from room temperature to 60° C.

Step (e)

The desired compound [I] wherein R is an unsubstituted aromatic heterocyclic or aryl group can be prepared by reduction of the compound [I] wherein the corresponding R is a halogen-substituted aromatic heterocyclic or aryl group. The reduction is preferably carried out under the same conditions as those of the reduction of the above Step (d).

Step (f)

The desired compound [I] wherein R is an unsubstituted aromatic heterocyclic or aryl group can be prepared by subjecting the compound [I] wherein the corresponding R is a lower alkylthio-substituted aromatic heterocyclic or aryl group to desulfurization. The desulfurization reaction is preferably carried out in the presence of a catalyst such as Raney nickel, palladium-carbon, etc., at a temperature from room temperature to 50° C.

Step (g)

The desired compound [I] wherein R is an aromatic heterocyclic or aryl group substituted by a formyl group, a hydroxy-substituted lower alkyl group, or a hydroxy- and aryl-substituted lower alkyl group can be prepared by subjecting the compound [I] wherein the corresponding R is a halogen-substituted aromatic heterocyclic or aryl group to lithiation, followed by reacting the product with a corresponding carbonyl compound (e.g. dimethylformamide, acetone, benzaldehyde, etc.). The lithiation is preferably carried out by using a lithiating agent such as n-butyl lithium, s-butyl lithium, t-butyl lithium, etc. The reaction is carried out at a temperature from −100° C. to 25° C.

Step (h)

The desired compound [I] wherein R is an amino-substituted aromatic heterocyclic or aryl group can be prepared by reduction of the compound [I] wherein the corresponding R is a nitro-substituted aromatic heterocyclic or aryl group. The reduction is carried out in the presence of a transition metal catalyst under hydrogen atmosphere, or by reacting with a reducing agent. The transition metal catalyst includes, for example, palladium-carbon, palladium-aluminum oxide, palladium-black, colloidal palladium, platinum oxide, Raney nickel, etc., and the reducing agent includes, for example, lithium aluminum hydride, tin, stannous chloride, zinc, iron, etc. The reaction is preferably carried out at a temperature from −20° C. to 80° C.

Step (i)

The desired compound [I] wherein R is a lower alkanoylamino-substituted or arylcarbonylamino-substituted aromatic heterocyclic or aryl group can be prepared by acylating the compound [I] wherein the corresponding R is an amino-substituted aromatic heterocyclic or aryl group. The acylating agent includes, for example, a carboxylic acid or a reactive derivative thereof (e.g. an acid chloride, an acid bromide, an acid anhydride, a mixed acid anhydride, etc.). When a free carboxylic acid is used, the reaction is preferably carried out in the presence of a condensing agent such as N,N'-dicyclohexylcarbodiimide, N-dimethylaminopropyl-N'-ethylcarbodiimide, diethylphosphoric cyanide, diphenylphosphoric azide, etc. When a reactive derivative of carboxylic acid is used, the reaction is preferably carried out in the presence of an acid acceptor such as an alkali metal hydroxide, an alkali metal hydrogen carbonate, an alkali metal carbonate, an organic base (e.g. triethylamine, pyridine, etc.), and the like. The reaction is preferably carried out at a temperature from −20° C. to 100° C.

Step (j)

The desired compound [I] wherein R is a mono- or di-lower alkylamino-substituted aromatic heterocyclic or aryl group can be prepared by subjecting the compound [I] wherein the corresponding R is an amino-substituted aromatic heterocyclic or aryl group to alkylation. The alkylation is carried out by (i) reacting in the presence of an acid acceptor with a lower alkyl halide (e.g. a lower alkyl chloride, a lower alkyl bromide, etc.) or a lower alkyl sulfonate (e.g. methanesulfonate, toluenesulfonate, etc.), and the like, or by (ii) subjecting a reaction product with a lower alkyl aldehyde to reduction in the presence of a reducing agent. The acid acceptor includes, for example, an alkali metal hydroxide, an alkali metal hydrogen carbonate, an alkali metal carbonate, an organic base (e.g. triethylamine, pyridine, etc.), and the like. The reducing agent includes, for example, sodium borohydride, sodium triacetoxyborohydride, formic acid, etc. The reaction is preferably carried out at a temperature from 0° C. to 100° C.

Step (k)

The desired compound [I] wherein R is a tetrazolyl-substituted aromatic heterocyclic or aryl group can be prepared by reacting the compound [I] wherein the corresponding R is a cyano-substituted aromatic heterocyclic or aryl group with tributyltin azide. The reaction is preferably carried out at a temperature from 50° C. to 120° C. Step (l):

The desired compound [I] wherein R is a protected or unprotected carboxyl-substituted lower alkoxy-substituted aromatic heterocyclic or aryl group can be prepared by reacting the compound [I] wherein the corresponding R is a hydroxy-substituted aromatic heterocyclic or aryl group with a protected or unprotected carboxyl-substituted lower alkyl halide or a protected or unprotected carboxyl-substituted lower alkyl sulfonate, etc. The reaction is preferably carried out in the presence of an acid acceptor such as an alkali metal hydroxide, an alkali metal hydrogen carbonate, an alkali metal carbonate, an organic base (e.g. triethylamine, pyridine, etc.). The reaction is preferably carried out at a temperature from 0° C. to 100° C. The protecting group for carboxyl group may be any conventional protecting groups for carboxyl group, and the protecting group can be removed by a conventional method which is selected according to the kind of the protecting group to be removed.

Step (m)

The desired compound [I] wherein R is a lower alkoxy-lower alkyl-substituted aromatic heterocyclic or aryl group can be prepared by halogenating the compound [I] wherein the corresponding R is a hydroxy-substituted lower alkyl-substituted aromatic heterocyclic or aryl group, followed by alkoxylating the product. The halogenating agent may be any halogenating agents used for Step (d). The reaction is preferably carried out at a temperature from −20° C. to 100° C. The alkoxylation reaction is carried out by reacting the product with a lower alcohol such as methanol, ethanol, isopropanol, etc. The alkoxylation reaction is preferably carried out in the presence of an acid acceptor, and the acid acceptor includes, for example, an alkali metal hydroxide, an alkali metal hydrogen carbonate, an alkali metal carbonate, an organic base (e.g. triethylamine, pyridine, etc.). The reaction is preferably carried out at a temperature from −20° C. to 100° C.

Step (n)

The desired compound [I] wherein R is a lower alkyl-sufinyl group and/or a lower alkyl sulfonyl group-substituted aromatic heterocyclic or aryl group can be prepared by reacting the compound [I] wherein the corresponding R is a lower alkylthio-substituted aromatic heterocyclic or aryl group in the presence of an oxidizing agent. The oxydizing agent is preferably 3-chloroperbenzoic acid, peracetic acid, hydrogen peroxide, pertrifluoroacetic acid, sodium periodate, sodim hypochlorite, potassium permanganate, and the like. The reaction is carried out at a temperature from 0° C. to 50° C.

Step (o)

The desired compound [I] wherein R is a lower alkylthio-substituted aromatic heterocyclic or aryl group can be prepared by reacting the compound [I] wherein the corresponding R is a lower alkylsufinyl-substituted aromatic heterocyclic or aryl group in the presence of an acid anhydride, subjecting the product to hydrolysis to give a thiol compound, followed by reacting the thiol compound with a lower alkyl halide in the presence of a base. The acid anhydride is preferably trifluoroacetic anhydride, acetic anhydride, and the like. The base is preferably potassium carbonate, sodium carbonate, a lower alkoxy sodium (e.g. sodium methoxide, sodium ethoxide, etc.), and the like. The reaction is preferably carried out at a temperature from 0° C. to 50° C.

Step (p):

The desired compound [I] wherein R is a cyano-substituted aromatic heterocyclic or aryl group can be prepared by reacting the compound [I] wherein the corresponding R is a halogen-substituted aromatic heterocyclic or aryl group with zinc cyanide in the presence of a catalyst. The catalyst is preferably the same catalysts for the above Process D. The reaction is preferably carried out at a temperature from 60° C. to 100° C.

Step (q)

The desired compound [I] wherein R is a trimethylsilyl-substituted lower alkynyl- or a hydroxy-substituted lower alkynyl-substituted aromatic heterocyclic or aryl group can be prepared by subjecting the compound [I] wherein the corresponding R is a halogen-substituted aromatic heterocyclic or aryl group to trimethylsilyl-substituted lower alkynylation, or to hydroxy-substituted lower alkynylation. The trimethylsilyl-substituted lower alkynylation, or the hydroxy-substituted lower alkynylation is carried out in the presence of a catalyst and an organic base. The catalyst is preferably the same catalysts for the above Process D, and the organic base is preferably the same organic bases for the above Step (i). The reaction can preferably proceed in the presence of a copper (I) salt like the above Process D. The reactions is carried out at a temperature from room temperature to 100° C.

Step (r)

The desired compound [I] wherein R is a lower alkynyl-substituted aromatic heterocyclic or aryl group can be prepared by reacting the compound [I] wherein the corresponding R is a trimethylsilyl-substituted lower alkynyl-substituted aromatic heterocyclic or aryl group in the presence of an acid or an inorganic base. The acid includes, for example, hydrochloric acid, sulfuric acid, hydrobromic acid, etc., and the base includes, for example, potassium carbonate, sodium carbonate, potassium hydroxide, sodium hydroxide, etc. The reaction is preferably carried out at a temperature from 0° C. to room temperature.

Step (s)

The desired compound [I] wherein R is a phenyl-lower alkyl-substituted aromatic heterocyclic or aryl group can be prepared by reacting the compound [I] wherein the corresponding R is a phenylalkenyl-substituted aromatic heterocyclic or aryl group in the presence of a catalyst. The catalyst may be the same catalysts used for the above Step (d). The reaction is preferably carried out at a temperature from room temperature to 60° C.

Step (t)

The desired compound [I] wherein Ring A and/or Ring B are a benzene ring substituted by formyl group can be prepared by reacting the compound [I] wherein the corresponding Ring A and/or Ring B are a benzene ring substituted by a di-lower alkoxy-substituted lower alkyl group in the presence of an acid. The acid includes, for example, an organic acid such as p-toluenesulfonic acid, oxalic acid, etc., and an inorganic acid such as hydrochloric acid, sulfuric acid, hydrobromic acid, etc. The reaction is preferably carried out at a temperature from 0° C. to 50° C.

Step (u)

The desired compound [I] wherein Ring A and/or Ring B are a benzene ring substituted by a lower alkoxycarbonyl-lower alkenyl group can be prepared by reacting the compound [I] wherein the corresponding Ring A and/or Ring B are a benzene ring substituted by formyl group with a triphenylphosphorane with a group to substitute. The reaction is preferably carried out at a temperature from room temperature for 60° C.

Step (v)

The desired compound [I] wherein Ring A and/or Ring B are a benzene ring substituted by a carboxy-substituted lower alkenyl group can be prepared by reacting the compound [I] wherein the corresponding Ring A and/or Ring B are a benzene ring substituted by a lower alkoxycarbonyl-lower alkenyl group in the presence of an inorganic base. The inorganic base includes, for example, sodium hydroxide, etc. The reaction is carried out at a temperature from 0° C. to room temperature.

Step (w)

The desired compound [I] wherein Q is a group of the formula: —SO— or —SO$_2$— can be prepared by reacting the compound [I] wherein the corresponding Q is a group of the formula: —S- in the presence of an oxidizing agent. The oxidizing agent includes, for example, 3-chloroperbenzoic acid, peracetic acid, hydrogen peroxide, pertrifluoroacetic acid, sodium periodate, sodium hypochorite, potassium permanganate, and the like. The reaction is preferably carried out at a temperature from 0° C. to 50° C.

The solvent used for the reactions of Steps (a) to (w) may be any one which does not affect the reaction, for example, dioxane, ethylene glycol dimethyl ether, dimethylacetamide, dimethylformamide, hexamethylphosphoramide, benzene, tetrahydrofuran, toluene, ethyl acetate, a lower alcohol, methylene chloride, chloroform, carbon tetrachloride, 1,3-dimethyl-2-imidazolidinone, acetic acid, diethyl ether, dimethoxyethane, dimethylsulfoxide, water, or a mixture thereof.

The starting compounds [II] and [VI] of the present invention may be prepared according to a method disclosed in Japanese Patent First Publication (Kokai) No. 155864/1993 or Japanese Patent First Publication (Kokai) No. 222003/1993. That is, the compound [II] wherein Q is a single bond may be prepared by treating a compound of the formula [X]:

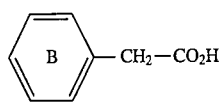 [X]

wherein Ring B is the same as defined above, with a halogenating agent (e.g. thionyl chloride, etc.), treating the resulting corresponding acid halide compound with an alcohol, followed by reacting the resulting ester compound with diethyl carbonate in the presence of a base (e.g. sodium hydride, potassium t-butoxide, etc.) to give a compound of the formula [XI]:

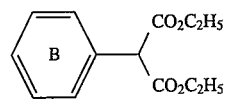 [XI]

wherein Ring B is the same as defined above. Further, the compound [XI] is treated with ammonia to give an amide compound of the formula:

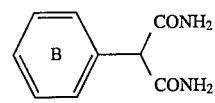

wherein Ring B is the same as defined above, followed by reacting the resulting compound with a compound of the formula:

wherein $R^1$ is the same as defined above, in the presence of a base (e.g. sodium ethylate, etc.) to give a compound of the formula [XII]:

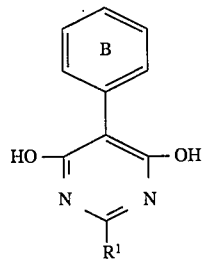 [XII]

wherein the symbols are the same as defined above, or the compound [XI] is reacted with an amidine compound of the formula [XIII]:

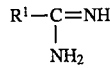 [XIII]

wherein $R^1$ is the same as defined above, in the presence of a base (e.g. sodium methoxide, etc.) to give the compound [XII]. Further, the hydroxy groups of the compound [XII] are converted into a reactive residue by treating with a halogenating agent (e.g. phosphorus oxychloride, etc.) to give a compound of the formula [XIV]:

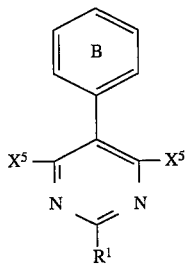 [XIV]

wherein $R^5$ is a reactive residue and the other symbols are the same as defined above, followed by reacting the resulting compound [XIV] with a compound of the formula [XV]:

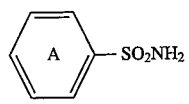 [XV]

wherein Ring A is the same as defined above, in the presence of an acid acceptor (e.g. sodium hydroxide, potassium hydroxide, potassium carbonate, sodium hydride, etc.).

On the other hand, the compound [II] wherein Q is a group of the formula: —O— may be prepared by reacting a compound of the formula [XVI]:

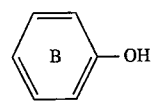 [XVI]

wherein Ring B is the same as defined above, with bromomalonic acid diethyl ester in the presence of an acid acceptor (e.g. potassium carbonate, etc.) to give a compound of the formula [XVII]:

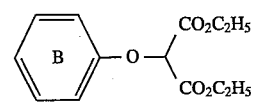 [XVII]

wherein Ring B is the same as defined above, followed by reacting the compound [XVII] with the amidine compound [XIII] in the presence of a base (e.g. sodium methoxide, etc.) to give a compound of the formula [XVIII]:

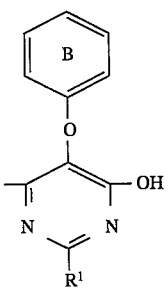 [XVIII]

wherein the symbols are the same as defined above, further by treating the compound [XVIII] in the same manner as the conversion reaction of the hydroxy groups of the compound [XII] into the reactive residues wherein Q is a single bond, to give a compound of the formula [XIX]:

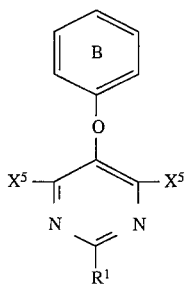

wherein the symbols are the same as defined above, and by treating the compound [XIX] in the same manner as the reaction of the compound [XIV] with the compound [XV].

Moreover, the compound [VI] may be prepared by reacting the corresponding compound [II] with a compound of the formula [XX]:

wherein Y, Alk and $Z^1$ are the same as defined above, in the presence of an acid acceptor (e.g. sodium hydride, etc.).

The starting compound [IV] of the present invention may be prepared, for example, by (i) reacting the compound [XIV] or the compound [XIX] with the compound [III] in the presence of an acid acceptor (e.g. sodium hydride, etc.) to give a compound [XXI]:

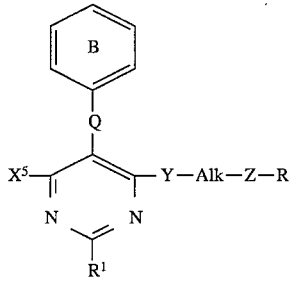

wherein the symbols are the same as defined above, reacting the product with sodium azide to give a compound of the formula [XXII]:

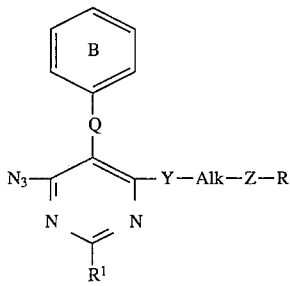

wherein the symbols are the same as defined above, followed by subjecting the product to catalytic hydrogenation, or by (ii) reacting the compound [XIV] or the compound [XIX] with ammonia to give a compound of the formula [XXIII]:

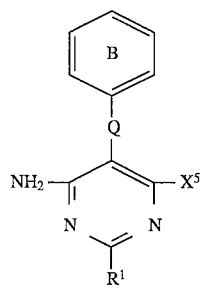

wherein the symbols are the same as defined above, followed by reacting the product with the compound [III] in the presence of an acid acceptor (e.g. sodium hydride, etc.).

Among the starting compounds [IV], the compound of the formula [IV] wherein Z is a group of the formula: —O— or —NH—, i.e. the compound of the formula [IV-a]:

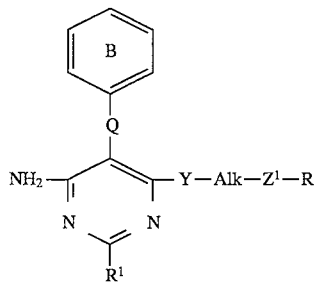

wherein the symbols are the same as defined above, may be prepared by (i) reacting the compound [XIV] or the compound [XIX] with the compound [XX] in the presence of an acid acceptor (e.g. sodium hydride, etc.) to give a compound [XXIV]:

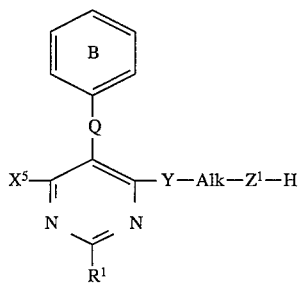

wherein the symbol are the same as defined above, reacting the product with sodium azide to give a compound of the formula [XXV]:

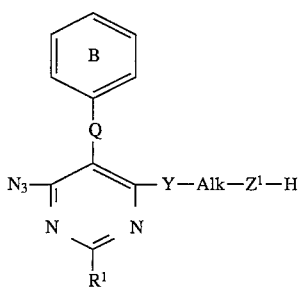

wherein the symbols are the same as defined above, subjecting the product into catalytic hydrogenation to give a compound [XXVI]:

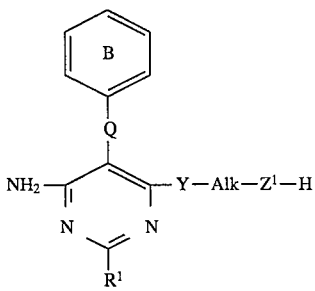
[XXVI]

wherein the symbols are the same as defined above, followed by reacting the product with the compound [VII] in the presence of an acid acceptor (e.g. sodium hydride, etc.), or by (ii) reacting the compound [XXIII] with the compound [XX] to give the compound [XXVI], followed by reacting the product with the compound [VII] in the presence of an acid acceptor (e.g. sodium hydride, etc.).

Moreover, the starting compound [VIII] may be prepared by (i) reacting a compound of the formula [XXVII]:

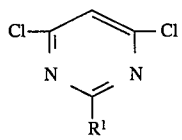
[XXVII]

wherein $R^1$ is the same as defined above, with the compound [XV] in the presence of an acid acceptor (e.g. sodium hydride, etc.) to give a compound of the formula [XXVIII]:

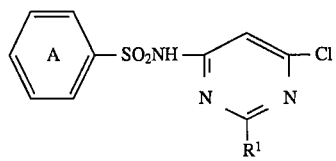
[XXVIII]

wherein the symbols are the same as defined above, reacting the product with the compound [III] in the presence of an acid acceptor (e.g. sodium hydride, etc.) to give a compound of the formula [XXIX]:

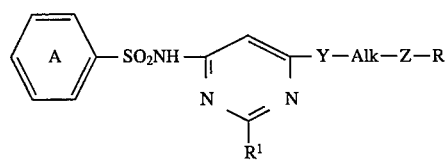
[XXIX]

wherein the symbols are the same as defined above, followed by forming a reactive residue by treating the compound [XXIX] with a halogenating agent, or by (ii) reacting the compound [XXVII] with the compound [III] in the presence of an acid acceptor (e.g. sodium hydride, etc.) to give a compound of the formula [XXX]:

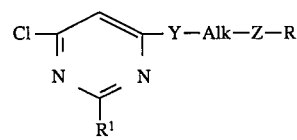
[XXX]

wherein the symbols are the same as defined above, reacting the compound [XXX] with sodium azide to give a compound of the formula [XXXI]:

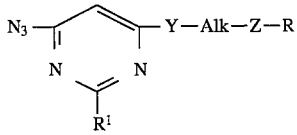
[XXXI]

wherein the symbols are the same as defined above, subjecting the compound [XXXI] to catalytic hydrogenation to give a compound [XXXII]:

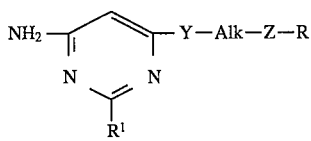
[XXXII]

wherein the symbols are the same as defined above, reacting the compound [XXXII] with the compound [V] in the presence of an acid acceptor (e.g. sodium hydride, etc.) to give the compound [XXIX], followed by forming a reactive residue by treating with a halogenating agent.

Among the starting compounds [VIII], the compound of the formula [VIII] wherein Z is a group of the formula: —O— or —NH—, i.e. the compound of the formula [VIII-a]:

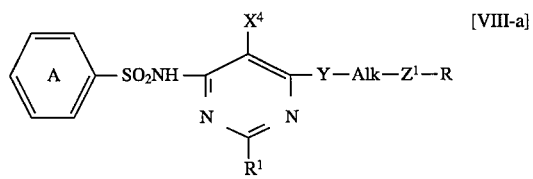
[VIII-a]

wherein the symbols are the same as defined above, may be prepared by (i) reacting the compound [XXVIII] with the compound [XX] in the presence of an acid acceptor (e.g. sodium hydride, etc.) to give a compound of the formula [XXXIII]:

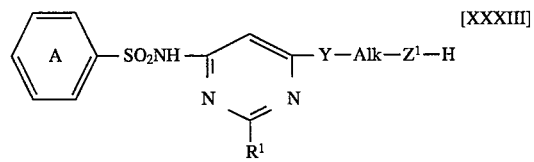
[XXXIII]

wherein the symbols are the same as defined above, followed by treating the compound [XXXIII] with a halogenating agent (e.g. N-bromosuccinimide, etc.) to form a reactive residue to give a compound of the formula [XXXIV]:

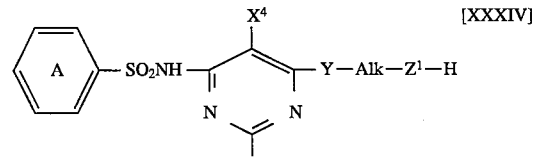
[XXXIV]

wherein the symbols are the same as defined above, followed by reacting the compound [XXXIV] with the compound [VII] in the presence of an acid acceptor (e.g. sodium hydride, etc.), or by (ii) reacting the compound [XXVII] with the compound [XX] in the presence of an acid acceptor (e.g. sodium hydride, etc.) to give a compound of the formula [XXXV]:

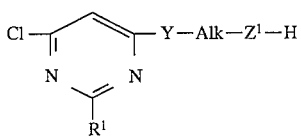

wherein the symbols are the same as defined above, reacting the compound [XXXV] with sodium azide to give a compound of the formula [XXXVI]:

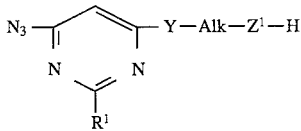

wherein the symbols are the same as defined above, followed by subjecting the compound [XXXVI] to catalytic hydrogenation to give a compound of the formula [XXXVII]:

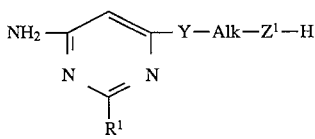

wherein the symbols are the same as defined above, reacting the compound [XXXVII] with the compound [V] to give a compound of the formula [XXXVIII]:

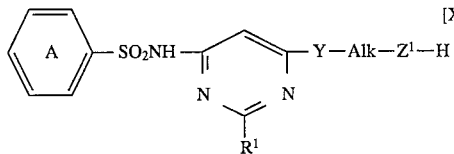

wherein the symbols are the same as defined above, treating the compound [XXXVIII] with a halogenating agent (e.g. bromine, etc.) to form a reactive residue to give the compound [XXXIV], followed by reacting the compound [XXXIV] with the compound [VII] in the presence of an acid acceptor (e.g. sodium hydride, etc.).

Throughout the present specification and claims, the lower alkyl group, the lower alkylthio group, the lower alkylamino group, the lower alkoxy group, the lower alkylenedioxy group, the lower alkylsulfinyl group, the lower alkylsulfonyl group and the lower alkylene group mean ones having 1 to 6 carbon atoms, especially ones having 1 to 4 carbon atoms, respectively. The lower alkenyl group, the lower alkanoyl group, the lower alkanoylamino group, the lower alkoxycarbonyl group, the lower alkynyl group, the lower alkenyloxy group, the N-lower alkylcarbamoyloxy group, the N-lower alkoxyiminomethyl group, the N-lower alkylaminocarbonyl group and the lower alkenylene group mean ones having 2 to 7 carbon atoms, especially ones having 2 to 5 carbon atoms, respectively. The cycloalkyl group means ones having 3 to 8 carbon atoms, especially having 3 to 6 carbon atoms. The halogen atom is chlorine, bromine, fluorine, or iodine.

The present invention is illustrated in more detail by the following Examples and Reference Examples, but should not be construed to be limited thereto.

EXAMPLE 1

To a stirred solution of pyridine-2-methanol (130 mg) in dimethylacetamide (0.5 ml) is added gradually with stirring sodium hydride (62.7% dispersion-type, 60 mg) under ice-cooling, and thereto is added 4-tert-butyl-N-{6-chloro-5-(3-methoxyphenoxy)pyrimidin-4-yl}benzenesulfonamide (100 mg). The mixture is reacted at 100° C. for 30 minutes, and cooled. The pH value of the mixture is adjusted to pH 8 with saturated aqueous ammonium chloride solution. The mixture is extracted with ethyl acetate, and the extract is washed, dried, and concentrated to dryness under reduced pressure. The residue is crystallized from ethyl acetate to give 4-tert-butyl-N-{5-(3-methoxyphenoxy)-6-(2-pyridinylmethoxy)pyrimidin-4-yl}benzenesulfonamide (110 mg) as crystals.

M.p. 206°–207.5° C.

EXAMPLES 2–18

The corresponding starting compounds are treated in the same manner as in Example 1 to give the compounds as listed in Tables 1–3.

TABLE 1

| Ex. No. | —Alk—Z—R | Physical Properties |
|---|---|---|
| 2 | (3-pyridylmethyl group structure) | M.p. 194–194° C. |
| 3 | (propyloxy-phenyl group structure) | M.p. 129–130° C. |
| 4 | (propyl-furan group structure) | M.p. 153.5–154° C. |
| 5 | (propyloxy-pyridyl group structure) | M.p. 159–160.5° C. |
| 6 | (propyloxy-methylphenyl group structure) | M.p. 118.5–120° C. |
| 7 | (pyrimidinyl group structure) | M.p. 148–149.5° C. |
| 8 | (propyloxy-bromophenyl group structure) | M.p. 130–131° C. |

TABLE 2

Structure: (CH₃)₃C-C₆H₄-SO₂NH-C(=N-CH=N-)-C(O-C₆H₄-CH₃)=C-O-Alk-Z-R (pyrimidine with 4-methylphenoxy and 4-tert-butylphenylsulfonamido substituents)

| Ex. No. | −Alk−Z−R | Physical Properties |
|---|---|---|
| 9 | −(CH₂)₂O−C₆H₄−C(CH₃)₃ | M.p. 167.5–169.5° C. |
| 10 | −(CH₂)₂O−C₆H₄−Br | M.p. 197–199.5° C. |
| 11 | −(CH₂)₂O−(2-naphthyl) | M.p. 249.5–251.5° C. |
| 12 | −(CH₂)₂O−C₆H₄−CH₂CH₃ | M.p. 118.5–120° C. |

TABLE 2-continued

| Ex. No. | −Alk−Z−R | Physical Properties |
|---|---|---|
| 13 | −(CH₂)₂O−C₆H₄−C(CH₃)₂ | M.p. 154.5–155.5° C. |
| 14 | −(CH₂)₂O−C₆H₄−OCH₃ | M.p.: 179.5–180° C. |
| 15 | −(CH₂)₂O−C₆H₄−OCH₂CH₃ | M.p. 183.5–184.5° C. |

TABLE 3

Structure: (CH₃)₃C-C₆H₄-SO₂NH-C(=N-CH=N-)-C(O-C₆H₄-CH₃)=C-O-Alk-Z-R

| Ex. No. | −Alk−Z−R | Physical Properties |
|---|---|---|
| 16 | −(CH₂)₂O−C₆H₄−OCH(CH₃)₂ | M.p.: 168–169° C. |
| 17 | −(CH₂)₂O−C₆H₄−OCH₂−C₆H₅ | M.p.: 153–154° C. |
| 18 | −(CH₂)₃−(3-pyridyl) | M.p.: 118–119° C. |

EXAMPLE 19

(1) After treating 4-tert-butyl-N-{6-chloro-5-(3-methoxyphenoxy)pyrimidin-4-yl}benzenesulfonamide and 2-aminoethanol in the same manner as in Example 1, the precipitated crystals are converted into a hydrochloride thereof to give N-{6-(2-aminoethoxy)-5-(3-methoxyphenoxy)pyrimidin-4-yl}-4-tert-butylbenzenesulfonamide hydrochloride (Compound A).

On the other hand, the mother liquor is purified by silica gel column chromatography (solvent; chloroform/methanol/acetic acid=10:1:0.3) and recrystallized from chloroform/diisopropyl ether to give 4-tert-butyl-N-{6-(2-hydroxyethylamino)-5-(3-methoxyphenoxy)pyrimidin-4-yl}benzenesulfonamide (Compound B).

Compound A: M.p. 201.5°–202° C.

Compound B: M.p. 161°–163° C.

(2) A mixture of Compound A (150 mg), 2-chloropyrimidine (61 mg), potassium carbonate (122 mg) and dimethylacetamide (1.5 ml) is heated with stirring at 100° C. for three days. The reaction solution is diluted with aqueous ammonium chloride solution, and extracted with ethyl acetate. The extract is washed and dried. The solvent is evaporated to remove the solvent, and the residue is purified by silica gel column chromatography (solvent; chloroform/methanol =100:1) and further recrystallized from ethyl acetate/n-hexane to give 4-tert-butyl-N-[5-(3-methoxyphenoxy)-6-{2-(2-pyrimidinylamino)ethoxy}-pyrimidin-4-yl]benzenesulfonamide hydrate (135 mg) as crystals.

M.p. 101°–102° C. (decomposed)

EXAMPLE 20

To a solution of Compound B (116 mg) obtained in Example 19-(1) in dimethylacetamide (2 ml) is added sodium hydride (60% dispersion-type, 33 mg), and thereto is added 2-chloropyrimidine (40 mg). The reaction solution is stirred at room temperature overnight, and the mixture is treated with saturated aqueous ammonium chloride solution, and extracted with ethyl acetate. The ethyl acetate layer is washed, dried, and evaporated to remove the solvent. The residue is purified by silica gel column chromatography (solvent; chloroform/methanol=20:1), and crystallized from chloroform/diisopropyl ether to give 4-tert-butyl-N-[5-(3-methoxyphenoxy)-6-{2-(pyrimidin-2-yloxy)ethylamino}pyrimidin-4-yl]benzenesulfonamide (125 mg) as crystals.

M.p. 147.5°–149° C.

EXAMPLE 21

To a solution of 4-tert-butyl-N-{6-(2-hydroxyethoxy)-5-(3-methoxyphenoxy)pyrimidin-4-yl}benzenesulfonamide (250 mg) in dimethylacetamide (5 ml) is added sodium hydride (60% dispersion-type, 64 mg) at room temperature, and the mixture is stirred for 20 minutes. To the reaction solution is added 5-bromo-2-chloropyrimidine (133 mg), and the mixture is stirred at room temperature for 18 hours. The reaction solution is poured into ice-water, and the mixture is neutralized with saturated aqueous ammonium chloride solution and extracted with ethyl acetate. The ethyl acetate layer is washed, dried, and evaporated to remove the solvent. The residue is purified by silica gel column chromatography (solvent; chloroform/methanol=40:1) to give crude crystals, which are recrystallized from ethyl acetate/diisopropyl ether to give N-[-6-{2-(5-bromopyrimidin-2-yloxy)ethoxy}-5-(3-methoxyphenoxy)pyrimidin-4-yl]-4-tert-butylbenzenesulfonamide (280 mg) as crystals.

M.p. 168°–168.5° C.

EXAMPLES 22–75

The corresponding starting compounds are treated in the same manner as in Example 21 to give the compounds as listed in Tables 4–11.

TABLE 4

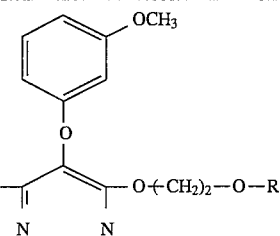

| Ex. No. | R | Physical Properties |
|---|---|---|
| 22 | 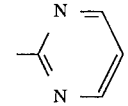 | M.p. 128–129.5° C. |
| 23 | 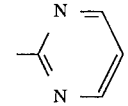 | M.p. 130.5–132° C. |
| 24 | 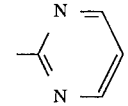 | M.p. 140.5–141.5° C. |
| 25 | 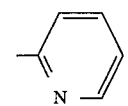 | M.p. 156–157° C. |
| 26 | 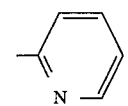 | M.p. 142–142.5° C. |
| 27 | 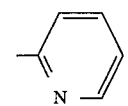 | M.p. 146.5–147° C. |
| 28 | 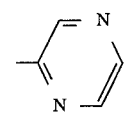 | M.p. 147.5–148.5° C. |
| 29 | 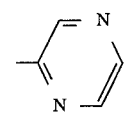 | M.p. 166–166.5° C. |

TABLE 5
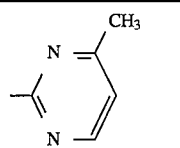
| Ex. No. | Alk | R | Physical Properties |
|---|---|---|---|
| 30 | —(CH$_2$)$_2$— | 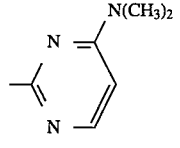 | M.p. 132–134.5° C. |
| 31 | —(CH$_2$)$_2$— | 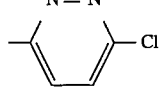 | M.p. 108–109° C. |
| 32 | —(CH$_2$)$_2$— | 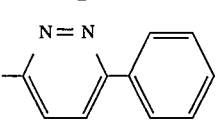 | M.p. 195.5–196° C. |
| 33 | —(CH$_2$)$_2$— | 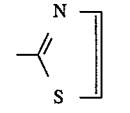 | M.p. 140.5–142° C. |
| 34 | —(CH$_2$)$_2$— | 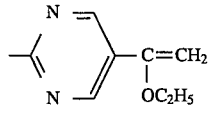 | M.p. 100.5–101° C. |
| 35 | —(CH$_2$)$_2$— | 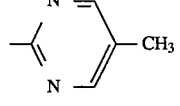 | M.p. 115.5–118° C. |
| 36 | —(CH$_2$)$_3$— | 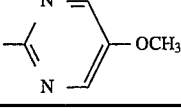 | M.p. 117–118.5° C. |
| 37 | —(CH$_2$)$_2$— | 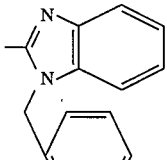 | M.p. 122–125° C. |
TABLE 6
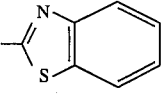
| Ex. No. | R | Physical Properties |
|---|---|---|
| 38 | 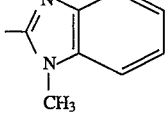 | M.p. 133.5–135.5° C. |
| 39 | 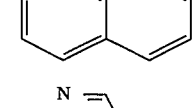 | M.p. 159–160° C. |
| 40 | 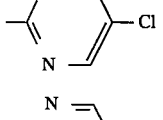 | M.p. 113–114° C. |
| 41 | 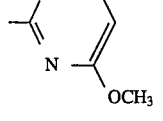 | M.p. 160–161° C. |
| 42 | 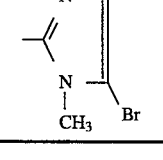 | M.p. 153.5–154.5° C. |
| 43 | | M.p. 122–123° C. |
| 44 | | M.p. 181.5–182.5° C. |

TABLE 7

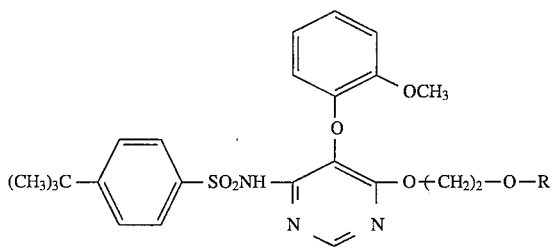

| Ex. No. | R | Physical Properties |
|---|---|---|
| 45 | (pyrimidine-Br) | M.p. 181.5–182.5° C. |
| 46 | (pyrimidine-SCH₃) | M.p. 156–157° C. |

TABLE 7-continued

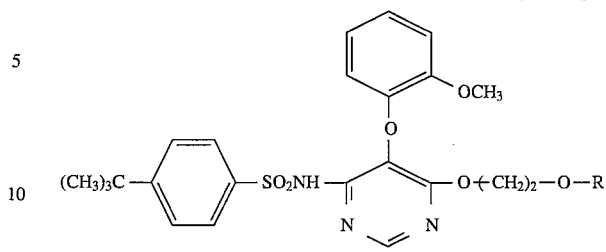

| Ex. No. | R | Physical Properties |
|---|---|---|
| 47 | (pyrimidine-OCH₃) | M.p. 186–187° C. |

TABLE 8

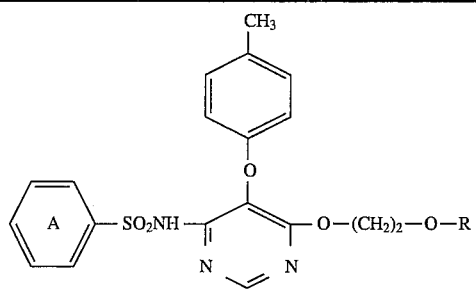

| Ex. No. | Ring A | R | Physical Properties |
|---|---|---|---|
| 48 | (CH₃)₃C–C₆H₄– | (pyrimidine-Br) | M.p. 167–168° C. Sodium salt: M.p. 238° C.~ (decomp) Potassium salt: M.p. >300° C. |
| 49 | (CH₃)₂CH–C₆H₄– | (pyridine) | M.p. 133–135° C. |
| 50 | (CH₃)₂CH–C₆H₄– | (pyrimidine-CH₃) | M.p. 168–169° C. |
| 51 | (CH₃)₂CH–C₆H₄– | (pyrimidine-Br) | M.p. 143–144° C. |
| 52 | (CH₃)₂CH–C₆H₄– | (pyrimidine) | M.p. 160–161° C. |

TABLE 8-continued
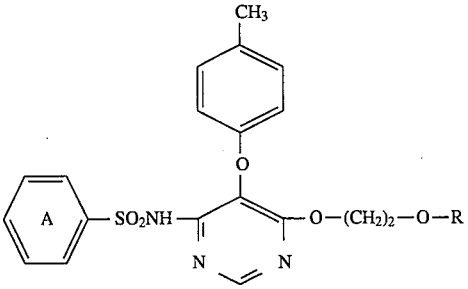
| Ex. No. | Ring A | R | Physical Properties |
|---|---|---|---|
| 53 | 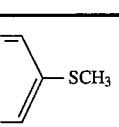 (CH$_3$)$_2$CH— | 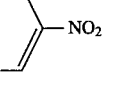 —SCH$_3$ | M.p. 194.5–195.5° C. <br> Sodium salt: <br> M.p. 165° C.~ |
| 54 | 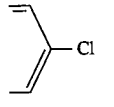 (CH$_3$)$_2$CH— | —NO$_2$ | M.p. 188–189° C. |
| 55 | (CH$_3$)$_2$CH— | 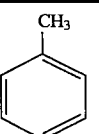 —Cl | M.p. 169.5–170.5° C. <br> Sodium salt: <br> M.p. 218° C.~ <br> (decomp) |
TABLE 9
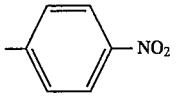
| Ex. No. | R | Physical Properties |
|---|---|---|
| 56 | 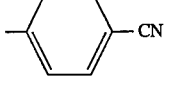 —NO$_2$ | M.p. 163–165° C. |
| 57 | —CN | M.p. 172 . 173° C. |
| 58 | 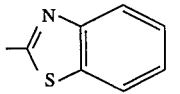 | M.p. 208.5–209.5° C. |
| 59 | 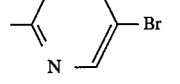 —Br | M.p. 178.5–179.5° C. |
TABLE 9-continued
| Ex. No. | R | Physical Properties |
|---|---|---|
| 60 | 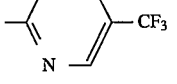 —CF$_3$ | M.p. 194–194.5° C. |
| 61 | 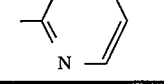 | M.p. 169–170° C. |

TABLE 10

[Structure: (CH3)3C-C6H4-SO2NH-[pyrimidine with 4-methylphenyl]-O-(CH2)2-O-R]

| Ex. No. | R | Physical Properties |
|---|---|---|
| 62 | 2-pyrimidinyl-OCH2-phenyl | M.p. 163–163.5° C. |
| 63 | 2-pyrimidinyl-CH3 | M.p. 180–182° C. |
| 64 | 2-pyrimidinyl-OCH3 | M.p. 188.5–189° C. Sodium salt: M.p. 148° C.~ |
| 65 | benzimidazol-1-yl-CH2-OCH3 | M.p. 138.5–139.5° C. |
| 66 | pyridyl-COONa Disodium salt | M.p. 285° C.~ |
| 67 | 2-pyrimidinyl-I | M.p. 203–204.5° C. |
| 68 | 2-pyrimidinyl-OCH2CH=CH2 | M.p. 147–148° C. |
| 69 | 2-pyrimidinyl-OCH2CN | M.p. 177–180° C. |
| 70 | 2-pyrimidinyl-OCH2-cyclopropyl | M.p. 144–146° C. |

TABLE 11

[Structure: (CH3)3C-C6H4-SO2NH-[pyrimidine with 4-methylphenyl]-O-(CH2)2-O-R]

| Ex. No. | R | Physical Properties |
|---|---|---|
| 71 | 2-pyrimidinyl-OCH(CH3)2 | M.p. 190–191° C. |
| 72 | 2-pyrimidinyl-OCH2-(2-pyridyl) | M.p. 177–178° C. |
| 73 | 2-pyrimidinyl-OC2H5 | M.p. 199–200° C. |
| 74 | 2-pyrimidinyl-OCH2-(2-thienyl) | M.p. 152–156° C. |
| 75 | 2-pyrimidinyl-CO2H | M.p. 222–225° C. |

EXAMPLE 76

A mixture of 6-[2-(5-bromopyrimidin-2-yloxy)ethoxy]-5-(4-methylphenyl)pyrimidin-4-amine (150 mg), 4-tert-amyl-benzenesulfonyl chloride (184 mg), 96% potassium hydroxide (powder, 300 mg), tetrabutylammonium hydrogen sulfate (34 mg) and toluene (10 ml) is stirred at room temperature overnight. The mixture is diluted with saturated aqueous ammonium chloride solution, and extracted with ethyl acetate. The ethyl acetate layer is washed, dried, and evaporated to remove the solvent. The residue is purified by silica gel column chromatography (solvent; chloroform/ethyl acetate=5:1), and recrystallized from hexane/ethyl acetate to give 4-tert-amyl-N-{6-[2-(5-bromopyridin-2-yloxy)ethoxy]-5-(4-methylphenyl)pyrimidin-4-yl}benzenesulfonamide (188 mg).

M.p. 153.5°–154.5° C.

IR (nujol, cm$^{-1}$): 3270, 1570, 1570, 1550

FABMS (m/z): 614, 612 (MH$^+$)

EXAMPLES 77–82

The corresponding starting compounds are treated in the same manner as in Example 76 to give the compounds as listed in Table 12.

TABLE 12

A—SO$_2$NH—C(=C(aryl-CH$_3$))—C(N=C(R$^1$)N)—O—(CH$_2$)$_2$—O—(pyrimidin-Br)

| Ex. No. | Ring A | R$^1$ | Physical Properties |
|---|---|---|---|
| 77 | (CH$_3$)$_3$C—phenyl— | —C(CH$_3$)$_2$ COOC(CH$_3$)$_3$ | M.p. 103–106° C. |
| 78 | I—phenyl— | H | M.p. 207.5–208° C. |
| 79 | 3,4-(CH$_3$O)$_2$—phenyl— | H | M.p. 180.5–182° C. |
| 80 | CF$_3$—phenyl— | H | M.p. 191.5–192.5° C. |
| 81 | CH$_3$O—phenyl— | H | M.p. 216.5–217.5° C. |
| 82 | Cl—phenyl— | H | M.p. 208–209° C. |

EXAMPLE 83

A mixture of 6-[2-(5-bromopyrimidin-2-yloxy)ethoxy]-5-(4-methylphenyl)pyrimidin-4-amine (150 mg), 4-bromobenzenesulfonyl chloride (191 mg), sodium iodide (112 mg), sodium hydride (60% dispersion-type, 45 mg) and tetrahydrofuran (5 ml) is stirred at room temperature overnight. To the mixture are added 4-bromobenzenesulfonyl chloride (191 mg) and sodium hydride (60% dispersion-type, 45 mg), and the mixture is refluxed overnight. After cooling, the reaction solution is treated with saturated ammonium chloride solution, and extracted with ethyl acetate. The ethyl acetate layer is washed, dried, and evaporated to remove the solvent. The residue is purified by preparative tin layer chromatography (solvent; chloroform/ethyl acetate=10:1) to give 4-bromo-N-{6o[2-(5-bromopyrimidin-2-yloxy)ethoxy]-5-(4-methylphenyl)pyrimidin-4-yl}benzenesulfonamide (85 mg).

M.p. 217°–218° C.

IR (nujol, cm$^{-1}$): 2800–2400, 1575, 1560

FABMS (m/z): 624, 622, 620 (MH$^+$)

EXAMPLE 84

A mixture of N-{5-bromo-6-[2-(5-methylthiopyrimidin-2-yloxy)ethoxy]pyrimidin-4-yl}-4-tert-butylbenzenesulfonamide (100 mg), 3,4-dimethoxyphenyltributyltin (220 mg), bis(triphenylphsophine)palladium (II) chloride (26 mg), copper (I) chloride (11 mg), a few crystals of 2,6-di-tert-butylcrezol and dioxane (5 ml) is refluxed for 1.5 hour. After cooling, the reaction solution is diluted with ethyl acetate and aqueous potassium fluoride solution, and the mixture is stirred at room temperature for 30 minutes. The insoluble materials are removed by filtration, and the filtrate is acidified with 10% hydrochloric acid, and the mixture is extracted with ethyl acetate. The ethyl acetate layer is washed, dried, and evaporated to remove the solvent. The residue is purified by preparative thin layer chromatography (solvent; chloroform/ethyl acetate=3:1), and recrystallized from ethyl acetate/diisopropyl ether to give 4-tert-butyl-N-{5-(3,4-dimethoxyphenyl)-6-[2-(5-methylthiopyrimidin-2- yloxy)ethoxy]-pyrimidin-4-yl}benzenesulfonamide (82 mg).

M.p. 170.5°–171.5° C.

IR (nujol, cm$^{-1}$): 3200, 1590, 1570, 1520, 1510

EXAMPLES 85–95

The corresponding starting compounds are treated in the same manner as in Example 84 to give the compounds as listed in Tables 13–14.

TABLE 13

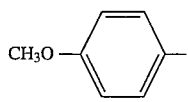

| Ex. No. | Ring B | Physical Properties |
|---|---|---|
| 85 | CH$_3$O—(4-phenyl)— | M.p. 166–167° C. |
| 86 | (3-CH$_3$O-phenyl)— | M.p. 126–129° C. |
| 87 | (3,4-methylenedioxyphenyl)— | M.p. 150–151° C. |
| 88 | CH$_3$O—C(=O)—(4-phenyl)— | M.p. 171–172° C. |
| 89 | (C$_2$H$_5$O)$_2$CH—(4-phenyl)— | M.p. 165.5–166.5° C. |
| 90 | C$_6$H$_5$—CH$_2$O—(4-phenyl)— | M.p. 150–152° C. |

TABLE 14

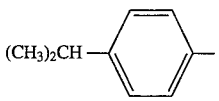

| Ex. No. | Ring B | Physical Properties |
|---|---|---|
| 91 | (CH$_3$)$_2$CH—(4-phenyl)— | M.p. 144.5–145.5° C. |

TABLE 14-continued

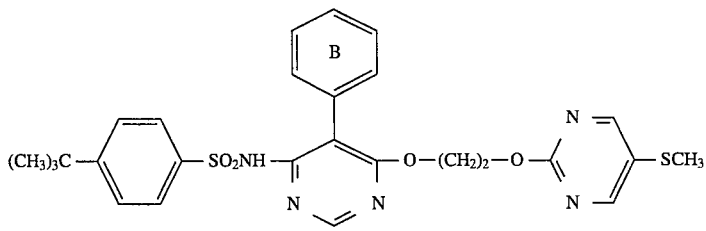

| Ex. No. | Ring B | Physical Properties |
|---|---|---|
| 92 | CF₃—C₆H₄— | M.p. 170–171° C. |
| 93 | Cl—C₆H₄— | M.p. 180.5–181.5° C. |
| 94 | C₂H₅—C₆H₄— | M.p. 157.5–159.5° C. |
| 95 | (CH₃)₃C—C₆H₄— | M.p. 164–166° C. |

EXAMPLE 96

A mixture of N-[6-{2-(5-bromopyridin-2-yloxy)ethoxy}-5-(3-methoxyphenoxy)pyrimidin-4-yl]-4-tert-butylbenzenesulfonamide (150 mg), tributylphenyltin (131 mg), bis(triphenylphosphine)palladium (II) chloride (8.5 mg) and dioxane (4 ml) is refluxed for 12 hours. The reaction solution is diluted with ethyl acetate, and treated with aqueous 10% potassium fluoride solution. The insoluble materials are removed by filtration, and the ethyl acetate layer is collected, washed with water, dried, and evaporated to remove the solvent. The residue is purified by silica gel column chromatography (solvent; chloroform), and recrystallized from ethyl acetate/diisopropyl ether to give 4-tert-butyl-N-[5-(3-methoxyphenoxy)-6-{2-(5-phenylpyrimidin-2-yloxy-)ethoxy}-pyrimidin-4-yl]benzenesulfonamide (85 mg) as crystals.

M.p. 160°–161° C.

EXAMPLES 97–118

N-[6-{2-(5-Bromopyrimidin-2-yloxy)ethoxy}-5-(4-methylphenyl)-pyrimidin-4-yl]-4-tert-butylbenzenesulfonamide and the corresponding starting compounds are treated in the same manner as in Example 96 to give the compounds as listed in Tables 15–17.

TABLE 15

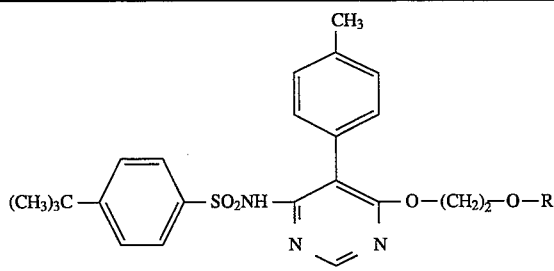

| Ex. No. | R | Physical Properties |
|---|---|---|
| 97 | pyrimidin-2-yl-furan | M.p. 197–198° C. Sodium salt: M.p. 254–256° C. (decomp) |
| 98 | pyrimidin-2-yl-pyridine | M.p. 185.5–186.5° C. |
| 99 | pyrimidin-2-yl-thiophene | M.p. 180.5–182° C. Sodium salt: M.p. 244–250° C. (decomp) |
| 100 | pyrimidin-2-yl-thiophene | M.p. 196–197° C. Sodium salt: M.p. 256–257° C. |

TABLE 15-continued

Structure: (CH₃)₃C-C₆H₄-SO₂NH-[pyrimidine with p-tolyl]-O-(CH₂)₂-O-R

| Ex. No. | R | Physical Properties |
|---|---|---|
| 101 | pyrimidin-2-yl-pyrazin-2-yl | M.p. 187–189° C. |
| 102 | pyrimidin-2-yl-pyridin-3-yl | M.p. 166–168° C. |
| 103 | pyrimidin-2-yl-(3-methoxyphenyl) | M.p. 190–190.5° C. |

TABLE 16

Structure: (CH₃)₃C-C₆H₄-SO₂NH-[pyrimidine with p-tolyl]-O-(CH₂)₂-O-R

| Ex. No. | R | Physical Properties |
|---|---|---|
| 104 | phenyl-thiophene | M.p. 186–187.5° C. |
| 105 | phenyl-furan | M.p. 186–187.5° C. |
| 106 | pyrimidin-2-yl-CH=CH-phenyl | M.p. 219.5–221° C. |
| 107 | pyrimidin-2-yl-(4-methoxyphenyl) | M.p. 194.5–195.5° C. |

TABLE 16-continued

| Ex. No. | R | Physical Properties |
|---|---|---|
| 108 | pyrimidin-2-yl-phenyl | M.p. 194.5–196° C. |
| 109 | pyridin-2-yl-thiophen-2-yl | M.p. 189.5–190.5° C. |
| 110 | pyridin-2-yl-furan-2-yl | M.p. 182–183° C. |
| 111 | pyridin-2-yl-(2-methoxyphenyl) | M.p. 126.5–128.5° C. |

TABLE 17

Structure: (CH₃)₃C-C₆H₄-SO₂NH-[pyrimidine with p-tolyl]-O-(CH₂)₂-O-R

| Ex. No. | R | Physical Properties |
|---|---|---|
| 112 | pyrimidin-2-yl-(5-methylthiophen-2-yl) | M.p. 181–182° C. |
| 113 | pyrimidin-2-yl-thiophen-2-yl | M.p. 148° C.~ |
| 114 | pyrimidin-2-yl-benzothiophen-2-yl | M.p. 219–220° C. |

TABLE 17-continued

Structure:
(CH₃)₃C—[phenyl]—SO₂NH—C(=C(—O—(CH₂)₂—O—R)—N=CH—N=)—[p-tolyl (CH₃)]

| Ex. No. | R | Physical Properties |
|---|---|---|
| 115 | pyrimidin-2-yl-furan group | M.p. 196–197° C. |
| 116 | pyrimidin-2-yl-(1-methylpyrrol-2-yl) group | M.p. 164–165.5° C. |
| 117 | pyrimidin-2-yl-(4,4-dimethyl-4,5-dihydrooxazol) group | M.p. 168–171° C. |
| 118 | pyrimidin-2-yl-(1-methylimidazol-2-yl) group | M.p. 176.5–177.5° C. |

EXAMPLE 119

N-[6-{2-(5-Bromopyrimidin-2-yloxy)ethoxy}-5-(2-methoxyphenoxy)pyrimidin-4-yl]-4-tert-butylbenzenesulfonamide and the corresponding starting compounds are treated in the same manner as in Example 96 to give 4-tert-butyl-N-[5-(2-methoxyphenoxy)-6-{2-(5-(2-thienyl)pyrimidin-2-yloxy)ethoxy}pyrimidin-4-yl]benzenesulfonamide.

M.p. 185.5°–186.5° C.

EXAMPLE 120

A mixture of 4-tert-butyl-N-[5-(3-methoxyphenoxy)-6-{2-(2-methylthiopyrimidin-4-yloxy)ethoxy}pyrimidin-4-yl]benzenesulfonamide (250 mg), Raney-nickel (W-2) (2 g) and ethanol (5 ml) is stirred at room temperature overnight, and the mixture is refluxed for four hours. Raney-nickel is removed by filtration, and washed with ethanol and acetic acid. The filtrate is concentrated under reduced pressure, and the residue is extracted with ethyl acetate. The ethyl acetate layer is washed, dried, and evaporated to remove the solvent. The residue is purified by silica gel column chromatography (solvent; chloroform/methanol- 10:1), and recrystallized from ethyl acetate/n-hexane to give 4-tert-butyl-N-[5-(3-methoxyphenoxy)-6-{2-(pyrimidin-4-yloxy)ethoxy}pyrimidin-4-yl]benzenesulfonamide (76 mg) as crystals.

M.p. 149°–150.5° C.

EXAMPLE 121

A mixture of 4-tert-butyl-N-[6-{2-(6-chloropyridazin-3-yloxy)ethoxy}-5-(3-methoxyphenoxy)pyrimidin-4-yl]benzenesulfonamide (150 mg), 10% palladium-carbon (30 mg), triethylamine (52 mg), methanol (8 ml) and tetrahydrofuran (6 ml) is stirred at room temperature for five hours under hydrogen atmosphere (1 atm), and the mixture is filtered to remove the catalyst. The filtrate is concentrated to dryness under reduced pressure. The residue is treated with aqueous citric acid solution, and extracted with chloroform. The extract is washed, dried and evaporated to remove the solvent. The residue is recrystallized from ethyl acetate/diisopropyl ether to give 4-tert-butyl-N-[5-(3-methoxyphenoxy)-6-{2-(pyridazin-3-yloxy)ethoxy}pyrimidin-4-yl]benzenesulfonamide (111 mg) as crystals.

M.p. 169.5°–170° C.

EXAMPLE 122

4-tert-buyl-N-[5-(3-methoxyphenoxy)-6-{2-(1-methyl-4,5-dibromoimidazol-2-yloxy)ethoxy}pyrimidin-4-yl]benzenesulfonamide and the corresponding starting compounds are treated in the same manner as in Example 121 to give 4-tert-buyl-N-[5-(3-methoxyphenoxy)-6-{2-(1-methylimidazol-2-yloxy)ethoxy}pyrimidin-4-yl]benzenesulfonamide.

M.p. 124°–126° C.

EXAMPLE 123

(1) To a solution of 2-mercaptoethanol (1.31 g) in dimethylacetamide (15 ml) is added sodium hydride (62.3% dispersion-type, 520 mg) under argon atmosphere. Five minutes later, to the mixture is added 4-tert-butyl-N-{6-chloro-5-(3-methoxyphenoxy)pyrimidin-4-yl}benzenesulfonamide (1.5 g), and the mixture is reacted under argon atmosphere at 70° C. for two hours, at 100° C. for three hours, and further reacted at 130° C. for two hours. The reaction solution is treated with hydrochloric acid, and extracted with ethyl acetate. The ethyl acetate layer is washed, dried, and evaporated to remove the solvent. The residue is purified by silica gel column chromatography (solvent; chloroform/methanol=70:1), and recrystallized from ethyl acetate/n-hexane to give 4-tert-butyl-N-{6-(2-hydroxyethylthio)-5-(3-methoxyphenoxy)pyrimidin-4-yl}benzenesulfonamide (1.14 g) as crystals.

M.p. 149.5°–150.5° C.

(2) A mixture of the above product (200 mg), 2-chloropyrimidine (61 mg), sodium hydride (62.3% dispersion-type, 47 mg), and dimethylacetamide (3 ml) is stirred at room temperature overnight. The mixture is treated with aqueous ammonium chloride solution, and extracted with ethyl acetate. The ethyl acetate layer is washed, dried, and evaporated to remove the solvent. The residue is purified by silica gel column chromatography (solvent; chloroform/methanol=50:1) and recrystallized from ethyl acetate/n-hexane to give 4-tert-butyl-N-[5-(3-methoxyphenoxy)-6-{2-(pyrimidin-2-yloxy)ethylthio}pyrimidin-4-yl]benzenesulfonamide (191 mg) as crystals.

M.p. 167.5°–168° C.

EXAMPLE 124

A mixture of 4-tert-butyl-N-[6-{2-(5-(1-ethoxyethenyl)pyrimidin-2-yloxy)ethoxy}- 5-(3-methoxyphenoxy)pyrimidin-4-yl]benzenesulfonamide (1.022 g), 10% hydrochloric acid (1 ml) and acetone (20 ml) is reacted at room temperature for four hours. The pH value of the reaction solution is adjusted to pH 6 with aqueous sodium hydrogen carbonate solution, and the mixture is evaporated to remove the solvent. To the residue are added aqueous ammonium chloride solution and ethyl acetate, and the ethyl acetate layer is collected. The ethyl acetate layer is washed, dried, and evaporated to remove the solvent. The residue is purified by silica gel column chromatography (solvent; ethyl acetate/ n-hexane=1:1~ethyl acetate), and recrystallized from ethyl acetate/n-hexane to give N-[6-{2-(5-acetylpyrimidin-2-yloxy)ethoxy}-5-(3-methoxyphenoxy)pyrimidin-4-yl]-4-tert-butylbenzenesulfonamide (849 mg).

M.p. 142.5°–144° C.

EXAMPLE 125

To a mixture of N-[6-{2-(5-acetylpyrimidin-2-yloxy)ethoxy}-5-(3-methoxyphenoxy)pyrimidin-4-yl]-4-tert-butylbenzenesulfonamide (756 mg), tetrahydrofuran (10 ml) and isopropyl alcohol (10 ml) is added with stirring sodium borohydride (48 mg) under ice-cooling, and the mixture is stirred for 40 minutes under ice-cooling. To the reaction solution is further added sodium borohydride (14 mg), and the mixture is stirred for 30 minutes. The mixture is diluted with water, and extracted with ethyl acetate. The ethyl acetate layer is washed, dried, and concentrated to dryness under reduced pressure. The residue is purified by silica gel column chromatography (solvent; chloroform/methanol= 40:1~20:1), and recrystallized from ethyl acetate/n-hexane to give 4-tert-butyl-N-[6-{2-(5-(1-hydroxyethyl)pyrimidin-2-yloxy)ethoxy}-5-(3-methoxyphenoxy)pyrimidin-4-yl]benzenesulfonamide (571 mg) as crystals.

M.p. 133°–135° C.

EXAMPLE 126

The corresponding starting compounds are treated in the same manner as in Example 125 to give 4-tert-butyl-N-[5-(4-hydroxymethyiphenyl)-6-{2-((5-methylthio)pyrimidin-2-yloxy)ethoxy}pyrimidin-4-yl]benzenesulfonamide.

M.p. 172°–173° C.

EXAMPLE 127

N-[6-{2-(4-Acetylphenoxy)ethoxy}-5-(4-methylphenyl)pyrimidin-4-yl]-4-tert-butylbenzenesulfonamide is treated in the same manner as in Example 125 to give 4-tert-butyl-N-[6-{2-(4-(1-hydroxyethyl)phenoxy)ethoxy}-5-(4-methylphenyl)pyrimidin-4-yl]benzenesulfonamide.

M.p. 176°–178° C.

EXAMPLE 128

To a solution of 4-tert-butyl-N-[6-{2-(5-(1-hydroxyethyl)pyrimidin-2-yloxy)ethoxy}-5-(3-methoxyphenoxy)pyrimidin-4-yl]benzenesulfonamide (150 mg) in methylene chloride (3 ml) is added thionyl chloride (90 mg), and the mixture is reacted at room temperature for 0.5 hour. The reaction solution is concentrated to dryness under reduced pressure, and to the residue are added 10% palladium-carbon (30 mg), triethylamine (76 mg) and ethanol (3 ml), and the mixture is stirred at room temperature for two hours under hydrogen atmosphere (1 atm). The catalyst is removed by filtration, and the filtrate is concentrated to dryness under reduced pressure. The residue is extracted with ethyl acetate, and the ethyl acetate layer is washed, dried, and evaporated to remove the solvent. The residue is purified by silica gel column chromatography (solvent; chloroform/ethyl acetate= 10:1), and recrystallized from ethyl acetate/n-hexane to give 4-tert-butyl-N-[6-{2-(5-ethylpyrimidin-2-yloxy)ethoxy}-5-(3-methoxyphenoxy)pyrimidin-4-yl]benzenesulfonamide (137 mg) as crystals.

M.p. 158.5°–159.5° C.

EXAMPLE 129

To a solution of N-[6-{2-(5-bromopyrimidin-2-yloxy)ethoxy}-5-(4-methylphenyl)pyrimidin-4-yl]-4-tert-butylbenzenesulfonamide (300 mg) in tetrahydrofuran (10 ml) is added a 1.6M solution of n-butyl lithium in n-hexane (0.75 ml) at −78° C. The mixture is stirred at −78° C. for 5 minutes, and thereto is added a solution of acetone (58 mg) in tetrahydrofuran (1 ml), and the mixture is warmed to room temperature. The mixture is treated with aqueous ammonium chloride solution, and extracted with ethyl acetate. The ethyl acetate layer is washed, dried, and evaporated to remove the solvent. The residue is purified by silica gel column chromatography (solvent; chloroform/ethyl acetate=2:1~1:1), and recrystallized from ethyl acetate/n-hexane to give 4-tert-butyl-N-[6-{2-(5-(1-hydroxy-1-methylethyl)primidin-2-yloxy)ethoxy}-5-(4-methylphenyl)pyrimidin-4-yl]benzenesulfonamide (88 mg) as crystals.

M.p. 149.5°–150.5° C.

EXAMPLE 130

N-[6-{2-(5-Bromopyrimidin-2-yloxy)ethoxy}-5-(4-methylphenyl)pyrimidin-4-yl]-4-tert-butylbenzenesulfonamide and benzaldehyde are treated in the same manner as in Example 129 to give 4-tert-butyl-N-[6-{2-(5-(α-hydroxybenzyl)primidin-2-yloxy)ethoxy}-5-(4-methylphenyl)pyrimidin-4-yl]benzenesulfonamide.

M.p. 183°–185° C.

EXAMPLES 131–133

A mixture of N-[6-{2-(4-bromophenoxy)ethoxy}-5-(4-methylphenyl)pyrimidin-4-yl]-4-tert-butylbenzenesulfonamide (600 mg), (1-ethoxyvinyl)tributyltin (680 mg), bis-(triphenylphosphine)palladium (II) chloride (35.5 mg) and dioxane (24 ml) is refluxed for 18 hours. The mixture is diluted with ethyl acetate, and thereto is added 10% aqueous potassium fluoride solution, and the precipitated crystals are removed by filtration. The filtrate is extracted with ethyl acetate, and the ethyl acetate layer is washed, dried, and concentrated to dryness under reduced pressure. The residue is purified by silica gel column chromatography (solvent; n-hexane/ethyl acetate=5:1~3:1~1:1), and the obtained compounds are each recrystallized from ethyl acetate/diisopropyl ether to give 4-tert-butyl-N-{5-(4-methylphenyl)-6-(2-phenoxyethoxy)pyrimidin-4-yl}benzenesulfonamide (Compound A) (42 mg), N-[6-{2-(4-acetylphenoxy)ethoxy}-5-(4-methylphenyl)pyrimidin-4-yl]-4-tert-butylbenzenesulfonamide (Compound B) (242 mg) and 4-tert-butyl-N-[6-{2-(4-ethoxycarbonylphenoxy)ethoxy}-5-(4-methylphenyl)pyrimidin-4-yl]benzenesulfonamide (Compound C) (58 mg), respectively.

Compound A: M.p. 186.5°–187.5° C.

Compound B: M.p. 205°–206.5° C.

Compound C: M.p. 199.5°–200.5° C.

EXAMPLE 134

To a solution of 4-tert-butyl-N-{5-(4-methylphenyl)-6-{2-(5-nitropyridin-2-yloxy)ethoxy}pyrimidin-4-yl}benzenesulfonamide (975 mg) in isopropanol/tetrahydrofuran (1:1) (20 ml) is added 10% palladium-carbon (200 mg), and the mixture is stirred at room temperature for 1.5 hour under hydrogen atmosphere (1 atm). The catalyst is removed by filtration, and the filtrate is concentrated under reduced pressure. The residue is purified by silica gel column chromatography (solvent; chloroform/ethyl acetate= 2:1), and recrystallized from ethyl acetate/n-hexane to give N-{6-{2-(5-aminopyridin-2-yloxy)ethoxy}-5-(4-methylphenyl)pyrimidin-4-yl}-4-tert-butylbenzenesulfonamide (829 mg) as crystals.

M.p. 165°–167° C. (decomposed)

EXAMPLE 135

To a solution of N-{6-{2-(5-aminopyridin-2-yloxy)ethoxy}-5-(4-methylphenyl)pyrimidin-4-yl}-4-tert-butyl-benzenesulfonamide (150 mg) in pyridine (2 ml) is added a solution of benzoyl chloride (43 mg) in methylene chloride (0.4 ml), and the mixture is stirred at room temperature for two hours. To the reaction solution is added 10% hydrochloric acid, and the mixture is extracted with ethyl acetate. The ethyl acetate layer is washed, dried and evaporated to remove the solvent. The residue is recrystallized from ethyl acetate/n-hexane to give N-(6-[2-{6-(4-tert-butylphenylsulfonylamino)-5-(4-methylphenyl)pyrimidin-4-yloxy}ethoxy]pyridin-3-yl)benzamide (161 mg) as crystals.

M.p. 173°–174.5° C.

EXAMPLE 136

N-{6-{2-(5-Aminopyridin-2-yloxy)ethoxy}-5-(4-methylphenyl)-pyrimidin-4-yl}-4-tert-butylbenzenesulfonamide and acetic anhydride are treated in the same manner as in Example 135 to give N-[6-[2-{6-(4-tert-butylphenylsulfonylamino)-5-(4-methylphenyl)pyrimidin-4-yloxy}ethoxy]pyridin-3-yl]acetamide.

M.p. 175°–176° C.

EXAMPLE 137

N-{6-{2-(5-Aminopyridin-2-yloxy )ethoxy}-5-(4-methylphenyl)-pyrimidin-4-yl}-4-tert-butylbenzenesulfonamide and pivaloyl chloride are treated in the same manner as in Example 135 to give N-[6-[2-{6-(4-tert-butylphenylsulfonylamino)-5-(4-methylphenyl)pyrimidin-4-yloxy}ethoxy]pyridin-3-yl]-pivalamide.

M.p. 140°–141° C.

EXAMPLE 138

A mixture of 4-tert-butyl-N-{6-[2-(4-benzyloxyphenoxy)ethoxy]-5-(4-methylphenyl)pyrimidin-4-yl}benzensulfonamide (3.95 g), 10% palladiumcarbon (1.5 g) and ethanol-tetrahydrofuran (80 ml–80 ml) is subjected to catalytic hydrogenation at room temperature under hydrogen atmosphere (1 atm) for 24 hours. The catalyst is removed by filtration, and the filtrate is concentrated. The residue is crystallized from ethyl acetate/diisopropyl ether to give 4-tert-butyl-N-{6-[2-(4-hydroxyphenoxy)ethoxy]-5-(4-methylphenyl)pyrimidin-4-yl}benzenesulfonamide (3.31 g).

M.p. 161.5°–163° C.

IR (nujol, cm$^{-1}$): 3260, 1590, 1570

FABMS (m/z): 556 (M$^+$+Na), 534 (MH$^+$)

EXAMPLE 139

The compound obtained in Example 62 is treated in the same manner as in Example 138 to give 4-tert-butyl-N-{6-[2-(5-hydroxypyrimidin-2-yloxy)ethoxy]-5-(4-methylphenyl)pyrimidin-4-yl}benzenesulfonamide.

M.p. 186.5°–188° C.

EXAMPLE 140

A mixture of 4-tert-butyl-N-{5-(4-methylphenyl)-6-[2-(4-nitrophenoxy)ethoxy]pyrimidin-4-yl}benzenesulfonamide (383 mg), 10% palladium-carbon (50 mg) and ethanol-tetrahydrofuran (6 ml–3 ml) is subjected to catalytic hydrogenation at room temperature under hydrogen atmosphere (1 atm) for two hours. The catalyst is removed by filtration, and the filtrate is concentrated. The residue is purified by silica gel column chromatography (solvent; chloroform/ethyl acetate=10:1), and recrystallized from ethyl acetate/diisopropyl ether to give N-{6-[2-(4-aminophenoxy)ethoxy]-5-(4-methylphenyl)pyrimidin-4-yl}-4-tert-butylbenzenesulfonamide (358 mg).

M.p. 190°–191° C.

IR (nujol, cm$^{-1}$): 3440, 3360, 3260, 1740, 1630, 1610

FABMS (m/z): 533 (MH$^+$)

EXAMPLE 141

To a solution of N-{6-[2-(4-aminophenoxy)ethoxy]-5-(4-methylphenyl)pyrimidin-4-yl}-4-tert-butylbenzenesulfonamide (100 mg) in tetrahydrofuran (2 ml) are added formic acid (38 mg) and 35% aqueous formaldehyde solution (0.05 ml), and the mixture is stirred at 50° C. for three hours. The reaction solution is poured into ice-water, and the mixture is neutralized with saturated aqueous sodium hydrogen carbonate solution, and extracted with ethyl acetate. The ethyl acetate layer is washed, dried and evaporated to remove the solvent. The residue is purified by silica gel column chromatography (solvent; chloroform/ethyl acetate=10:1), and recrystallized from ethyl acetate/diisopropyl ether to give 4-tert-butyl-N-{6-[2-(4-dimethylaminophenoxy)ethoxy]-5-(4-methylphenyl)pyrimidin-4-yl}benzenesulfonamide (67 mg).

M.p. 142°–145° C.

IR (nujol, cm$^{-1}$): 3260, 1590, 1570

FABMS (m/z): 561 (MH$^+$)

EXAMPLE 142

A mixture of 4-tert-butyl-N-{6-[2-(4-cyanophenoxy)ethoxy]-5-(4-methylphenyl)pyrimidin-4-yl}benzensulfonamide (1.31 g), tributyltin azide (1.60 g) and toluene (13 ml) is refluxed under argon atmosphere for 24 hours. After cooling, ethyl acetate and 10% aqueous potassium fluoride solution are added to the reaction solution. The insoluble materials are removed by filtration, and the ethyl acetate layer is concentrated to dryness under reduced pressure. To the residue are added 10% aqueous sodium hydroxide solution and diethyl ether, and the mixture is stirred at room temperature for 20 minutes. The aqueous layer is washed with diethyl ether, and acidified with 10% hydrochloric acid under ice-cooling. The mixture is extracted with ethyl acetate, and the ethyl acetate layer is washed, dried and evaporated to remove the solvent. The residue is purified by silica gel column chromatography (solvent: chloroform: methanol=100: 0~20:1), and crystallized from ethyl acetate to give 4-tert-butyl-N-{5-(4-methylphenyl)-6-[2-(4-(5-tetrazolyl)phenoxy)ethoxy]-pyrimidin- 4-yl}benzensulfonamide (1.26 g).

M.p. 165°–166° C.

IR (nujol, cm$^{-1}$): 3260, 1620, 1580

FABMS (m/z): 586 (MH$^+$)

EXAMPLE 143

To a solution of 4-tert-butyl-N-{6-[2-(4-hydroxyphenoxy)ethoxy]-5-(4-methylphenyl)pyrimidin-4-yl}benzenesulfonamide (200 mg) in dimethylformamide (2 ml) is added sodium hydride (60% dispersion-type, 32 mg), and the mixture is stirred at room temperature for 30 minutes. To the mixture is added a solution of tert-butyl bromoacetate (77 mg) in dimethylformamide (2 ml) under ice-cooling, and the mixture is stirred at the same temperature for one hour. The reaction solution is poured into ice-water, and treated with saturated aqueous ammonium chloride solution, and extracted with ethyl acetate. The ethyl acetate layer is washed, dried and evaporated to remove the solvent. The residue is purified by silica gel column chromatography (solvent; hexane/ethyl acetate=3:1), and crystallized from ethyl acetate/diisopropyl ether to give tert-butyl 4-{2-(6-(4-tert-butybenzenesulfonylamino)-5-(4-methylphenyl)pyrimidin-4-yloxy)ethoxy}phenoxyacetate (225 mg).

M.p. 129.5°–130.5° C.

IR (nujol, cm$^{-1}$): 3280, 1765, 1590, 1570

FABMS (m/z): 648 (MH$^+$)

EXAMPLE 144

To a solution of tert-butyl 4-{2-{6-(4-tert-butylbenzenesulfonylamino)-5-(4-methylphenyl)pyrimidin-4-yloxy]ethoxy}phenoxyacetate (1.25 g) in dichloromethane (120 ml) are added anisole (2.09 g) and trifluoroacetic acid (20 ml) under ice-cooling. The mixture is stirred at room temperature for five hours, washed with water, and extracted with 10% aqueous sodium hydroxide solution. The aqueous layer is washed with chloroform, and acidified with 10% hydrochloric acid under ice-cooling. The mixture is extracted with ethyl acetate, and the extract is washed, dried, and evaporated to remove the solvent. The residue is crystallized from ethyl acetate/diisopropyl ether to give 4-{2-[6-(4-tert-butylbenzenesulfonylamino )-5-(4-methylphenyl)pyrimidin-4-yloxy]ethoxy}phenoxyacetic acid (1.14 g).

M.p. 183°–184.5° C.

IR (nujol, cm$^{-1}$): 3260, 3240, 1760, 1740, 1710, 1580, 1565

FABMS (m/z): 592 (MH$^+$)

EXAMPLE 145

To a solution of 4-tert-butyl-N-{6-[2-(4-(1-hydroxyethyl)phenoxy)ethoxy]-5-(4-methylphenyl)pyrimidin-4-yl}benzenesulfonamide (85 mg) in dichloromethane (3 ml) is added thionyl chloride (54 mg), and the mixture is stirred for one hour. The reaction solution is concentrated to dryness under reduced pressure, and the residue is dissolved in ethanol-tetrahydrofuran (6 ml –2 ml). To the mixture is added triethylamine (45 mg) at room temperature, and the mixture is stirred for three hours. The mixture is evaporated to remove the solvent, and the residue is dissolved in ethyl acetate, washed, dried and evaporated to remove the solvent. The residue is purified by silica gel column chromatography (solvent; hexane/ethyl acetate=3:1), and recrystallized from ethyl acetate/diisopropyl ether to give 4-tert-butyl-N-{6-[2-(4-(1-ethoxyethyl)phenoxy)ethoxy]-5-(4-methylphenyl)pyrimidin-4-yl}benzenesulfonamide (61 mg).

M.p. 139°–140° C.

IR (nujol, cm$^{-1}$): 3270, 1610, 1590, 1570

FABMS (m/z): 590 (MH$^+$)

EXAMPLE 146

To a solution of N-[6-{2-(5-bromopyrimidin-2-yloxy)ethoxy}-5-(4-methylphenyl)pyrimidin-4-yl]-4-tert-butyl-benzenesulfonamide (700 mg) in tetrahydrofuran (15 ml) is added dropwise a 1.6 M solution of n-butyl lithium in n-hexane (1.46 ml) at –78° C. The mixture is stirred at –78° C. for 15 minutes, and thereto is added dimethylformamide (0.28 ml), and the reaction solution is reacted at the same temperature for 15 minutes. The solution is treated with aqueous ammonium chloride solution, and acidified with 10% hydrochloric acid, and extracted with ethyl acetate. The ethyl acetate layer is washed, dried, and the residue is purified by silica gel column chromatography (solvent; chloroform/ethyl acetate=100:1~30:1), and recrystallized from diisopropyl ether to give 4-tert-butyl-N-[6-{2-(5-formylpyrimidin-2-yloxy)ethoxy}-5-(4-methylphenyl)pyrimidin-4-yl]benzenesulfonamide (198 mg) as crystals.

M.p. 191°–193° C.

FABMS (m/z): 548 (MH$^+$)

EXAMPLE 147

To a solution of 4-tert-butyl-N-[6-{2-(5-formylpyrimidin-2-yloxy)ethoxy}-5-(4-methylphenyl)pyrimidin-4-yl]benzenesulfonamide (143 mg) in tetrahydrofuran-isopropanol (4 ml–4 ml) is added sodium borohydride (13 mg) under ice-cooling, and the mixture is reacted for two hours. The mixture is treated with aqueous ammonium chloride solution, and extracted with ethyl acetate. The ethyl acetate layer is washed, dried, and evaporated to remove the solvent. The residue is purified by silica gel column chromatography (solvent; chloroform/methanol=200:1~50:1), and crystallized from diethyl ether to give 4-tert-butyl-N-[6-{2-(5-hydroxymethylpyrimidin-2-yloxy)ethoxy}-5-(4-methylphenyl)pyrimidin-4-yl]benzenesulfonamide (96 mg).

M.p. 172°–173° C.

FABMS (m/z): 550 (MH$^+$)

EXAMPLE 148

To a suspension of sodium hydride (0.25 g) in tetrahydrofuran (5 ml) is added dropwise a solution of 4-tert-butyl-N-[6-(2-hydroxyethoxy)-5-(4-methylphenyl)-2-n-propylpyrimidin-4-yl]benzenesulfonamide (1.00 g) in dimethylacetamide (3 ml) and tetrahydrofuran (10 ml) at room temperature, and thereto is added 2-chloro-5-bromopyrimidine (0.56 g), and the mixture is stirred at room temperature for 2.5 hours. The reaction mixture is acidified with ice-cold diluted hydrochloric acid, and extracted with ethyl acetate. The extract is washed, dried, and evaporated to remove the solvent. The resulting oily product is purified by silica gel column chromatography (solvent; chloroform), and crystallized from n-hexane to give 4-tert-butyl-N-[6-{2-(5-bromopyrimidin-2-yloxy)ethoxy}-5-(4-methylphenyl)-2-n-propylpyrimidin-4-yl]benzenesulfonamide (1.21 g) as crystals.

M.p. 184°–186° C.

EXAMPLES 149–189

The corresponding starting compounds are treated in the same manner as in Example 148 to give the compounds as listed in Tables 18–25.

TABLE 18

Structure: (CH$_3$)$_3$C—[phenyl]—SO$_2$NH—C(=N–C(R$^1$)=N–)—C(—O—[2-methoxyphenyl])=C—O—(CH$_2$)$_2$—O—R

| Ex. No. | R$^1$ | R | Physical Properties |
|---|---|---|---|
| 149 | 2-pyrimidinyl | pyrimidin-5-yl (2-thienyl substituted) | M.p. 154–156° C. |
| 150 | 2-pyrimidinyl | 5-bromopyrimidin-2-yl | M.p. 216–218° C. (decomposed) |
| 151 | 2-pyrimidinyl | 5-(SCH$_3$)pyrimidin-2-yl | M.p. 219–221° C. |
| 152 | —CH$_2$CH$_2$CH$_3$ | pyrimidin-5-yl (2-thienyl substituted) | M.p. 103–104° C. |
| 153 | —CH$_2$CH$_2$CH$_3$ | 5-bromopyrimidin-2-yl | M.p. 143–145° C. |
| 154 | 2-pyrimidinyl | 4-NO$_2$-phenyl | M.p. 214–215° C. |

TABLE 19

Structure: (CH$_3$)$_3$C—[phenyl]—SO$_2$NH—C(=N–C(R$^1$)=N–)—C(—O—[2-methoxyphenyl])=C—O—(CH$_2$)$_2$—O—R

| Ex. No. | R$^1$ | R | Physical Properties |
|---|---|---|---|
| 155 | 2-pyrimidinyl | 5-OCH$_3$-pyrimidin-2-yl | M.p. 140–142° C. |
| 156 | 2-pyrimidinyl | 5-Cl-pyrimidin-2-yl | Amorphous |
| 157 | 2-pyrimidinyl | 5-NO$_2$-pyridin-2-yl | Amorphous |
| 158 | 2-pyrimidinyl | pyrimidin-5-yl (2-furyl substituted) | Amorphous |
| 159 | 2-pyrimidinyl | pyrimidin-5-yl (2-thienyl substituted) | M.p. 223–232° C. |
| 160 | piperazin-1-yl (N–H) | pyrimidin-5-yl (2-thienyl substituted) | — |
| 161 | 4-methylpiperazin-1-yl | 5-bromopyrimidin-2-yl | — |

TABLE 20

Structure: (CH₃)₃C-C₆H₄-SO₂NH-C(pyrimidine with R¹)=C(O-C₆H₄-o-OCH₃)-... -O-(CH₂)₂-O-R

| Ex. No. | R¹ | R | Physical Properties |
|---|---|---|---|
| 162 | 2-pyrimidinyl | 5-iodo-2-pyrimidinyl | M.p. 187–191° C. |
| 163 | —CH₃ | 5-bromo-2-pyrimidinyl | M.p. 148–149.5° C. |
| 164 | 4-morpholinyl | 5-bromo-2-pyrimidinyl | M.p. 178–180° C. |
| 165 | 4-morpholinyl | 5-(2-thienyl)-2-pyrimidinyl | M.p. 147–149° C. |
| 166 | 4-methyl-1-piperazinyl | 5-(2-thienyl)-2-pyrimidinyl | — |

TABLE 21

Structure: (CH₃)₃C-C₆H₄-SO₂NH-C(pyrimidine with R¹)=C(p-tolyl)-... -O-(CH₂)₂-O-R

| Ex. No. | R¹ | R | Physical Properties |
|---|---|---|---|
| 167 | 2-pyrimidinyl | 5-(2-thienyl)-2-pyrimidinyl | M.p. 199–206° C. |
| 168 | 2-pyrimidinyl | 5-bromo-2-pyrimidinyl | M.p. 133–136° C. |
| 169 | phenyl | 5-bromo-2-pyrimidinyl | M.p. 173.5–174.5° C. |
| 170 | —CH(CH₃)₂ | 5-(2-thienyl)-2-pyrimidinyl | M.p. 202–203° C. |
| 171 | —CH(CH₃)₂ | 5-bromo-2-pyrimidinyl | M.p. 166–168° C. |
| 172 | 2-thienyl | 5-(2-thienyl)-2-pyrimidinyl | M.p. 196–197° C. |
| 173 | 2-thienyl | 5-bromo-2-pyrimidinyl | M.p. 209–210° C. |
| 174 | 2-pyridyl | 5-(2-thienyl)-2-pyrimidinyl | M.p. 185–187.5° C. |
| 175 | 2-pyridyl | 5-bromo-2-pyrimidinyl | M.p. 169–171.5° C. |

TABLE 22

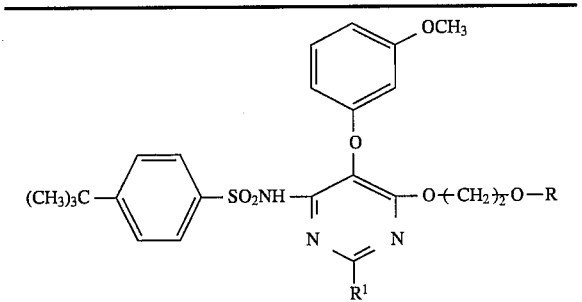

| Ex. No. | R¹ | R | Physical Properties |
|---|---|---|---|
| 176 | 2-pyrimidinyl | (pyrimidin-5-yl)methylidene-thiophene | M.p. 175–177° C. |
| 177 | 2-pyrimidinyl | 5-bromopyrimidin-4-yl methylidene | M.p. 132–141° C. |

TABLE 23

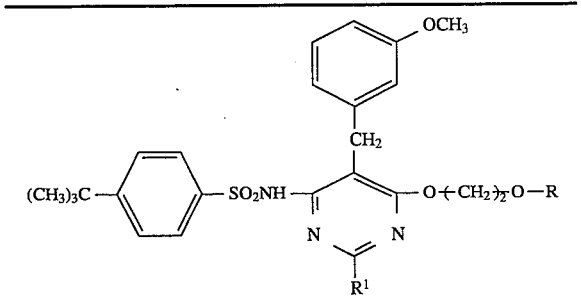

| Ex. No. | R¹ | R | Physical Properties |
|---|---|---|---|
| 178 | 2-pyrimidinyl | 5-bromopyrimidin-4-yl methylidene | M.p. 228–229.5° C. |
| 179 | 2-pyrimidinyl | (pyrimidin-5-yl)methylidene-thiophene | M.p. 233.5–234.5° C. |

TABLE 24

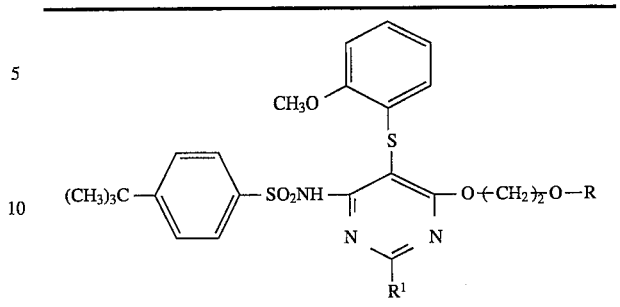

| Ex. No. | R¹ | R | Physical Properties |
|---|---|---|---|
| 180 | H | 5-bromopyrimidin-4-yl methylidene | M.p. 141–142° C. |
| 181 | H | (pyrimidin-5-yl)methylidene-thiophene | M.p. 183–184.5° C. |
| 182 | 2-pyrimidinyl | 5-bromopyrimidin-4-yl methylidene | M.p. 194.5–196° C. |

TABLE 25

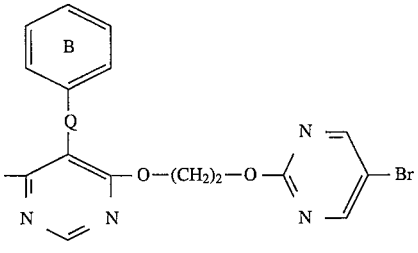

| Ex. No. | Ring A | —Q—⟨B⟩ | Physical Properties |
|---|---|---|---|
| 183 | 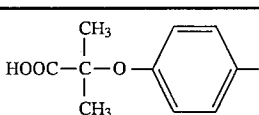 | 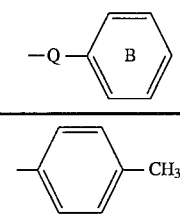 | M.p. 161–163° C. |
| 184 | 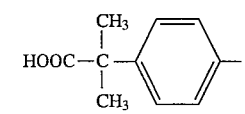 | 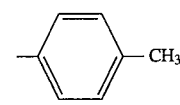 | M.p. 130–137° C. |
| 185 | 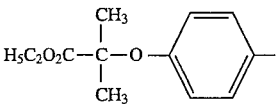 | 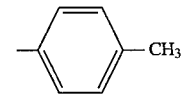 | M.p. 130–132° C. |
| 186 | 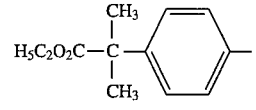 | 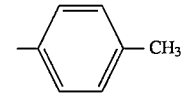 | M.p. 155–156° C. |
| 187 | 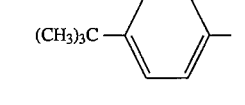 | 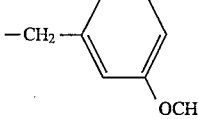 | M.p. 164–165.5° C. |
| 188 | 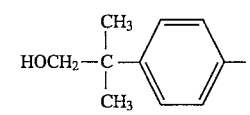 | 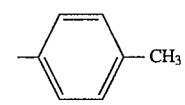 | M.p. 167–170° C. |
| 189 | 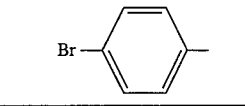 | 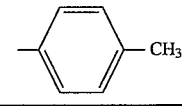 | M.p. 217–218° C. |

EXAMPLE 190

A mixture of 4-tert-butyl-N-[6-{2-(5-bromopyrimidin-2-yloxy)ethoxy}-5-(4-methylphenyl)-2-n-propylpyrimidin-4-yl]benzenesulfonamide (300 mg), 2-thienyltributyltin (670 mg), bis(triphenylphosphine)palladium (II) chloride (16 mg) and dioxane (5 ml) is refluxed for 80 minutes. After cooling, the reaction solution is diluted with ethyl acetate, and thereto is added 10% aqueous potassium fluoride solution. The mixture is stirred at room temperature for one hour, and the reaction solution is washed, dried, and evaporated to remove the solvent. The residue is purified by silica gel column chromatography (solvent; n-hexane/ethyl acetate= 30:1~10:1), and crystallized from methylene chloride/n-hexane to give 4-tert-butyl-N-[6-{2-(5-(2-thienyl)pyrimidin-2-yloxy)ethoxy}-5-(4-methylphenyl)-2-n-propylpyrimidin-4-yl]benzenesulfonamide (209 mg) as crystals.

M.p. 165°–166° C.

EXAMPLE 191

The product obtained in Example 150 and 2-pyridyltributyltin are treated in the same manner as in Example 190 to give 4-tert-butyl-N-[6-{2-(5-(2-pyridyl)pyrimidin-2-yloxy)ethoxy}-5-(2-methoxyphenoxy)-2-(2-pyrimidyl)pyrimidin-4-yl]benzenesulfonamide.

M.p. 149°–157° C.

EXAMPLE 192

(1) To a solution of N-{6-chloro-2-(2-pyrimidyl)-5-(2-methoxyphenoxy)pyrimidin-4-yl}-4-tert-butylbenzenesulfonamide (1.05 g) and 2-(4-acetylphenoxy)ethanol (728 mg) in dimethylacetamide (12 ml) is added sodium hydride (240 mg) under ice-cooling, and the mixture is stirred at room temperature overnight. The reaction solution is acidified with 10% hydrochloric acid, and extracted with ethyl acetate. The extract is washed, dried, and evaporated to remove the solvent. The residue is purified by silica gel column chromatography (solvent; chloroform/acetonitrile= 2:1), and recrystallized from ethyl acetate/n-hexane to give N-[6-{2-(4-acetylphenoxy)ethoxy}-2-(2-pyrimidyl)-5-(2-methoxyphenoxy)pyrimidin-4-yl}-4-tert-butylbenzenesulfonamide (482 mg) as crystals.

M.p. 169°–172° C.

(2) To a mixture of the above product (197 mg), isopropyl alcohol (2 ml) and tetrahydrofuran (2 ml) is added sodium borohydride (26 mg) under ice-cooling, and the mixture is stirred at the same temperature for two hours. After the reaction is complete, the mixture is evaporated to remove the solvent, and the residue is acidified with 10% hydrochloric acid, and extracted with ethyl acetate. The extract is washed, dried, and evaporated to remove the solvent. The residue is purified by silica gel column chromatography (solvent; chloroform/acetonitrile=1:1) and recrystallized from ethyl acetate/n-hexane to give N-{6-{2-(4-(1 -hydroxyethyl)phenoxy)ethoxy}-2-(2-pyrimidyl)-5-(2-methoxyphenoxy)pyrimidin-4-yl}-4-tert-butylbenzenesulfonamide (85 mg) as crystals.

M.p. 191°–194° C.

EXAMPLE 193

N-{6-Chloro-2-(2-pyrimidyl)-5-(2-methoxyphenoxy)pyrimidin-4-yl}-4-tert-butylbenzenesulfonamide and 2-(4-bromophenoxy)ethanol are treated in the same manner as in Example 192-(1) to give N-{6-{2-(4-bromophenoxy)ethoxy}-2-(2-pyrimidyl)-5-(2-methoxyphenoxy)pyrimidin-4-yl}-4-tert-butylbenzenesulfonamide.

M.p. 251°–256° C.

EXAMPLE 194

To a stirred solution of sodium 4-tert-butyl-N-{6-[2-(5-methylthiopyrimidin-2-yloxy)ethoxy]-5-(4-methylphenyl)pyrimidin-4-yl}benzenesulfonamide (1.0 g) in chloroform (10 ml) is added 3-chloroperbenzoic acid (412 mg) at 0° C., and the reaction mixture is stirred at 0° C. for one hour, and stirred at room temperature overnight. The reaction mixture is diluted with saturated aqueous sodium hydrogen carbonate solution, and extracted three times with chloroform. The combined organic layer is washed with brine, dried over sodium sulfate, filtered, and concentrated under reduced pressure. The residue is purified by silica gel column chromatography (solvent; chloroform/ethyl acetate= 2:1 .- 1:1), and the desired fractions are recrystallized from ethyl acetate/n-hexane to give 4-tert-butyl-N-{6-[2-(5-methylsulfonylpyrimidin-2-yloxy)ethoxy]-5-(4-methylphenyl)pyrimidin-4-yl}benzenesulfonamide (Compound A) (91 mg) and 4-tert-butyl-N-{6-[2-(5-methylsulfinylpyrimidin-2-yloxy)ethoxy]-5-(4-methylphenyl)pyrimidin-4-yl}benzenesulfonamide (Compound B) (601 mg).

Compound A: Colorless crystalline powder M.p. 170°–172° C.

Compound B: Colorless crystalline powder M.p. 206.5°–208° C.

EXAMPLE 195

(1) A solution of 4-tert-butyl-N-{6-[2-(5-methylsulfinylpyrimidin-2-yl-oxy)ethoxy]-5-(4-methylphenyl)pyrimidin-4-yl}benzenesulfonamide (471 mg) in trifluoroacetic anhydride (5 ml) and methylene chloride (5 ml) is refluxed for 30 minutes, and the mixture is evaporated to remove the solvent. The residue is dissolved in methanol/triethylamine (1:1) (20 ml), and concentrated to dryness under reduced pressure. The residue is dissolved in chloroform, washed with saturated aqueous ammonium chloride solution and brine, dried over sodium sulfate, and filtered. The filtrate is concentrated under reduced pressure to give 4-tert-butyl-N-{6-[2-(5-mercaptopyrimidin-2-yloxy)ethoxy]-5-(4-methylphenyl)pyrimidin-4-yl}benzenesulfonamide as pale yellow foam (529 mg).

(2) A mixture of the above product (200 mg), potassium carbonate (100 mg), ethyl iodide (97 mg) and dimethylformamide (4 ml) is stirred at room temperature for two hours under argon atmosphere, and diluted with 10% hydrochloric acid. The mixture is extracted with ethyl acetate, and the organic layer is washed with water (twice), and brine, and dried over sodium sulfate, filtered, and concentrated under reduced pressure. The residue is purified by preparative thin layer chromatography (solvent; chloroform/ethyl acetate= 15:1) and recrystallized from ethyl acetate/n-hexane to give 4-tert-butyl-N-{6-[2-(5-ethylthiopyrimidin-2-yloxy)ethoxy]-5-(4-methylphenyl)pyrimidin-4-yl}benzenesulfonamide (90 mg) as colorless crystalline powder.

M.p. 177°–178° C.

EXAMPLE 196

The corresponding starting compounds are treated in the same manner as in Example 195 to give 4-tert-butyl-N-{6-[2-(5-isopropylthiopyrimidin-2-yloxy)ethoxy]-5-(4-methylphenyl)pyrimidin-4-yl}benzenesulfonamide.

M.p. 161.5°–162.5° C.

EXAMPLE 197

A mixture of 4-tert-butyl-N-{6-[2-(5-bromopyrimidin-2-yloxy)ethoxy]-5-(4-methylphenyl)pyrimidin-4-yl}benzenesulfonamide (1.00 g), zinc cyanide (784 mg), tetrakis(triphenylphosphine)palladium (250 mg) and 1,3-dimethyl-2-imidazolidinone (40 ml) is stirred at 80° C. for 6 hours under argon atmosphere. The mixture is cooled to room temperature, and diluted with saturated aqueous ammonium chloride solution. The mixture is extracted with ethyl acetate, and the organic layer is washed with water (twice) and brine, dried over sodium sulfate, and filtered. The filtrate is concentrated under reduced pressure, and the residue is purified by silica gel column chromatography (solvent; chloroform/ethyl acetate=10:1) and recrystallized from tetrahydrofuran/ethyl acetate to give 4-tert-butyl-N-{6-[2-(5-cyanopyrimidin-2-yloxy)ethoxy]-5-(4-methylphenyl)pyrimidin-4-yl}benzenesulfonamide (590 mg) as colorless crystalline powder.

M.p. 196°–197° C.

EXAMPLE 198

A mixture of 4-tert-butyl-N-{6-[2-(5-bromopyrimidin-2-yloxy)ethoxy]-5-(4-methylphenyl)pyrimidin-4-yl}benzenesulfonamide (1.00 g), trimethylsilylacetylene (330 mg), bis(triphenylphosphine)palladium (II) chloride (58 mg), copper (I) iodide (32 mg), triethylamine (420 mg) and dimethylformamide (5 ml) is stirred at 50° C. for three hours under argon atmosphere, and cooled to room temperature. The mixture is diluted with saturated aqueous ammonium chloride solution, and extracted with ethyl acetate. The organic layer is washed with water and brine, and dried over sodium sulfate, filtered, and concentrated under reduced pressure. The residue is purified by silica gel column chromatography (solvent; chloroform/ethyl acetate=40:1), and recrystallized from ethyl acetate/n-hexane to give 4-tert-butyl-N-{6-[2-(5-trimethylsilylethynylpyrimidin-2-yloxy)ethoxy]-5-(4-methylphenyl)pyrimidin-4-yl}benzenesulfonamide (837 mg) as colorless crystalline powder.

M.p. 200°–202° C.

EXAMPLE 199

The corresponding starting compounds are treated in the same manner as in Example 198 to give 4-tert-butyl-N-{6-[2-(5-(3-hydroxy-3-methyl- 1 -butynyl)pyrimidin-2-yloxy)ethoxy]-5-(4-methylphenyl)pyrimidin-4-yl}benzenesulfonamide.

M.p. 172.5°–173.5° C.

EXAMPLE 200

A mixture of 4-tert-butyl-N-{6-[2-(5-trimethylsilylethynylpyrimidin-2-yloxy)ethoxy]-5-(4-methylphenyl)pyrimidin-4-yl}benzenesulfonamide (667 mg), potassium carbonate (299 mg) and dry methanol (13 ml) is stirred at 0° C. for two hours, and diluted with saturated aqueous ammonium chloride solution, and extracted with ethyl acetate. The organic layer is washed with water and brine, dried over sodium sulfate, and filtered. The filtrate is concentrated under reduced pressure, and the residue is purified by silica gel column chromatography (solvent; chloroform/ethyl acetate=30:1) to give 4-tert-butyl-N-{6-[2-(5-ethynylpyrimidin-2-yloxy)ethoxy]-5-(4-methylphenyl)pyrimidin-4-yl}benzenesulfonamide (502 mg) as colorless crystalline powder.

M.p. 207°–210° C.

EXAMPLE 201

A mixture of 4-tert-butyl-N-{6-[2-(5-methylthiopyrimidin-2-yloxy)ethoxy]-5-(4-diethoxymethyl]phenyl)pyrimidin-4-yl}benzenesulfonamide (558 mg), p-toluenesulfonic acid hydrate (50 mg), tetrahydrofuran (18 ml) and water (6 ml) is stirred at room temperature for one hour. The mixture is evaporated to remove the solvent, and the residue is diluted with ethyl acetate. The ethyl acetate layer is washed with water and brine, dried over sodium sulfate, filtered, and concentrated under reduced pressure. The residue is purified by silica gel column chromatography (solvent; chloroform/ethyl acetate=2:1) and recrystallized from chloroform/ethyl acetate to give 4-tert-butyl-N-{6-[2-(5-methylthiopyrimidin-2-yloxy)ethoxy]-5o(4-formylphenyl)pyrimidin-4-yl}benzenesulfonamide (345 mg) as colorless crystalline powder.

M.p. 223°–224° C.

EXAMPLE 202

A mixture of 4-tert-butyl-N-{6-[2-(5-methylthiopyrimidin-2-yloxy)ethoxy]-5-(4-formylphenyl)pyrimidin-4-yl}benzenesulfonamide (269 mg), (carbethoxyethylidene)triphenylphosphorane (242 mg) and chloroform (5 ml) is stirred at room temperature for four hours, and the mixture is diluted with chloroform, washed with 10% hydrochloric acid, water, and brine. The mixture is dried over sodium sulfate, filtered, and concentrated under reduced pressure. The residue is purified by silica gel column chromatography (solvent; hexane/ethyl acetate=1:1), and recrystallized from ethyl acetate/n-hexane to give ethyl (E)-3-{4-[4-(4-tert-butylphenylsulfonylamino)-6-[2-(5-methylthiopyrimidin-2-yloxy)ethoxy]pyrimidin-5-yl]}phenylacrylate (261 mg) as colorless crystalline powder.

M.p. 172°–173° C.

EXAMPLE 203

A mixture of ethyl (E)-3-{4-[4-(4-tert-butylphenylsulfonylamino)-6-[2-(5-methylthiopyrimidin-2-yloxy)ethoxy]pyrimidin-5-yl]}phenylacrylate (182 mg), 1N sodium hydroxide solution (0.56 ml), tetrahydrofuran (3 ml) and water (1 ml) is stirred at room temperature for 30 hours, and diluted with chloroform. The mixture is acidified with 10% aqueous hydrochloric acid solution. The mixture is extracted twice with chloroform, and the organic layer is washed with brine, dried over sodium sulfate, filtered, and concentrated under reduced pressure. The residue is purified by preparative thin layer chromatography (solvent; chloroform/methanol=10:1), and crystallized from ethyl acetate/n-hexane to give (E)-3-{4-[4-(4-tert-butylphenylsulfonylamino)- 6-[2-(5-methylthiopyrimidin-2-yloxy)ethoxy] pyrimidin-5-yl]} phenylacrylic acid (31 mg) as colorless crystalline powder.

M.p. 196°–204° C.

EXAMPLE 204

The corresponding starting compounds are treated in the same manner as in Example 203 to give 4-[4-(4-tert-butylbenzenesulfonamido)-6-[2-(5-methylthiopyrimidin-2-yloxy)ethoxy]pyrimidin-5-yl]benzoic acid.

M.p. 226°–227° C.

EXAMPLES 205–206

To a stirred solution of 4-tert-butyl-N-{6-[2-(5-bromopyrimidin-2-yloxy)ethoxy]-5-(2-methoxyphenylthio)pyrimidin-4-yl}benzenesulfonamide (464 mg) in chloroform (9 ml) is added 3-chloroperbenzoic acid (217 mg) at 0° C., and the mixture is stirred at 0° C. for two hours. The reaction mixture is diluted with saturated aqueous sodium hydrogen carbonate solution and extracted three times with chloroform. The organic layer is washed with brine, dried over sodium sulfate, and filtered. The filtrate is concentrated under reduced pressure. The residue is purified by preparative thin layer chromatography (solvent; chloroform/ethyl acetate=10:1). The eluated less polar fractions are combined and recrystallized from methylene chloride/ethyl acetate to give 4-tert-butyl-N-{6-[2-(5-bromopyrimidin-2-yloxy)ethoxy]-5-(2-methoxyphenylsulfonyl)pyrimidin-4-yl}benzenesulfonamide (197 mg) as colorless crystalline powder.

M.p. 208°–21 0° C.

Separately, the more polar fractions are combined and crystallized from ethyl acetate/n-hexane to give 4-tert-butyl-N-{6-[2-(5-bromopyrimidin-2-yloxy)ethoxy]-5-(2-methoxyphenylsulfinyl)pyrimidin-4-yl}benzenesulfonamide (167 mg) as colorless crystalline powder.

M.P. 163°–164.5° C.

EXAMPLE 207

To a suspension of sodium hydride (65 mg) in dimethylacetamide (0.5 ml) and tetrahydrofuran (0.5 ml) is added dropwise a solution of 4-(2-hydroxy-1,1-dimethylethyl)-N-{6-[2-hydroxyethoxy]-5-(4-methylphenyl)pyrimidin-4-yl}benzenesulfonamide (135 mg) in dimethylacetamide (2 ml) and THF (2 ml) solution over period of 5 minutes at room temperature, and thereto is added 5-bromo-2-chloropyrimidine (399 mg). The mixture is stirred at room temperature for 6 days. The reaction mixture is acidified with cold diluted hydrochloric acid, and extracted with ethyl acetate. The organic layer is washed with water and saturated brine, dried over anhydrous sodium sulfate, and evaporated to remove the solvent. The oily residue is purified by silica gel column chromatography (solvent; chloroform/ ethyl acetate=100:1), and evaporated to remove the solvent. The resulting crude crystals are recrystallized from methylene chloride/isopropyl ether to give 4-[2-(5-bromopyrimidin-2-yloxy)-1, 1 -dimethylethyl]-N-{6-[2-(5-bromopyrimidin-2-yloxy)ethoxy]-5-(4-methylphenyl)pyrimidin-4-yl}benzenesulfonamide (77 mg) as colorless crystals.

M.p. 156°–158° C.

chromatography (solvent; chloroform/ethyl acetate=50:1), and the fractions are evaporated to remove the solvent. The resulting crude crystals are recrystallized from methylene chloride/isopropyl ether to give 4-tert-butyl-N-{6-[2-(5-(5-bromopyrimidin-2-yloxy)pyrimidin-2-yloxy)ethoxy]-5-(4-methylphenyl)pyrimidin-4-yl}benzenesulfonamide (238 mg) as colorless needles.

M.p. 183°–184° C.

EXAMPLES 209–213

The corresponding starting compounds are treated in the same manner as in Example 208 to give the compounds as listed in Table 26.

TABLE 26

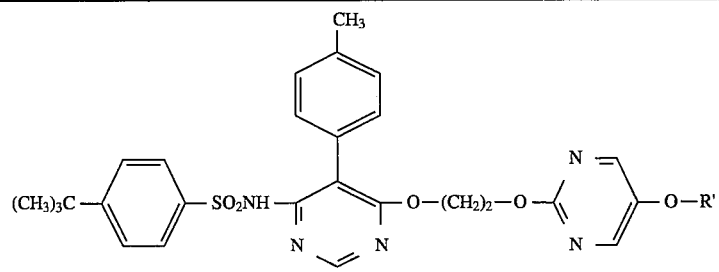

| Ex. No. | R' | Physical Properties |
|---|---|---|
| 209 | benzothiazol-2-yl | M.p. 191–192° C. |
| 210 | 4,5-dibromo-1-methylimidazol-2-yl | M.p. 119–120° C. |
| 211 | pyrimidin-2-yl | M.p. 137–138° C. |
| 212 | thiazol-2-yl | M.p. 166–168° C. |
| 213 | —CONHCH$_3$ | M.p. 84–88° C. |

EXAMPLE 208

To a solution of 4-tert-butyl-N-{6-[2-(5-hydroxypyrimidin-2-yloxy)ethoxy]-5-(4-methylphenyl)pyrimidin-4-yl}benzenesulfonamide (200 mg) in dimethylformamide (4 ml) is added potassium carbonate (154 mg), 5-bromo-2-chloropyrimidine (216 mg), and the mixture is stirred at 50° C. for two hours. The reaction mixture is acidified with cold hydrochloric acid, and extracted with ethyl acetate. The organic layer is washed with water and brine, and dried over anhydrous sodium sulfate, and evaporated to remove the solvent. The oily residue is purified by silica gel column

EXAMPLE 214

A mixture of 4-tert-butyl-N-{6-[2-(5-(α-styryl)pyrimidin-2-yloxy)ethoxy]-5-(4-methylphenyl)pyrimidin-4-yl}benzenesulfonamide (130 mg), 10% palladium-carbon (42 mg), ethanol (1 ml) and tetrahydrofuran (10 ml) is stirred at room temperature under hydrogen atmosphere for one hour. The catalyst is removed by filtration, and the filtrate is concentrated under reduced pressure. The residue is purified by preparative tin layer chromatography (solvent; chloroform/ethyl acetate=15:1), and crystallized from ethyl acetate/diisopropyl ether to give 4-tert-butyl-N-{6-[2-(5-(α- phenethyl)pyrimidin-2-yloxy)ethoxy]-5-(4-methylphenyl)pyrimidin-4-yl}benzenesulfonamide (111 mg) as colorless needles.

M.p. 158.5°–160.5° C.

Reference Example 1

To 1,3-propanediol (7 ml) is added sodium hydride (60% dispersion-type, 312 mg), and thereto is added 4-tert-butyl-N-{6-chloro-5-(3-methoxyphenoxy)pyrimidin-4-yl}benzenesulfonamide (707 mg). The reaction mixture is reacted at 90° C. for two hours, and then reacted at 130° C. for one hour. The reaction solution is acidified with 10% hydrochloric acid, and extracted with ethyl acetate, and the ethyl acetate layer is washed, dried, and concentrated to dryness under reduced pressure. The residue is purified by silica gel column chromatography (solvent; chloroform/ethyl acetate=10:1), and crystallized from ethyl acetate/diisopropyl ether to give 4-tert-butyl-N-{6-(3-hydroxypropyloxy)-5-(3-methoxyphenoxy)pyrimidin-4-yl}benzenesulfonamide (315 mg) as crystals.

M.p. 113°–114° C.

Reference Examples 2–12

The corresponding starting compounds are treated in the same manner as in Reference Example 1 to give the compounds as listed in Tables 27–28.

TABLE 27

| Ref. Ex. No. | Ring A | $R^1$ | Physical Properties |
|---|---|---|---|
| 2 | HOCH₂–C(CH₃)₂–C₆H₄– | H | M.P. 182–185° C. |
| 3 | HOOC–C(CH₃)₂–C₆H₄– | H | M.P. 189–191° C. |
| 4 | HOOC–C(CH₃)₂–O–C₆H₄– | H | M.P. 188–190° C. |
| 5 | CH₃–C(CH₃)₂–C₆H₄– | 2-pyridyl | M.P. 247° C. (decom.) |

TABLE 27-continued

| Ref. Ex. No. | Ring A | $R^1$ | Physical Properties |
|---|---|---|---|
| 6 | CH₃–C(CH₃)₂–C₆H₄– | –(CH₂)₂CH₃ | M.P. 121–122° C. |
| 7 | CH₃–C(CH₃)₂–C₆H₄– | 2-pyrimidinyl | M.P. 211–216° C. |

TABLE 28

| Ref. Ex. No. | Ring B | Q | $R^1$ | Physical Properties |
|---|---|---|---|---|
| 8 | 3-OCH₃-C₆H₄– | –CH₂– | 2-pyrimidinyl | M.p. 109–110° C. |
| 9 | 2-CH₃O-C₆H₄– | –O– | morpholino | M.p. 124–126.5° C. |
| 10 | 2-CH₃O-C₆H₄– | –O– | 4-methylpiperazino | MS (m/z): 572 (MH⁺) |

TABLE 28-continued

| Ref. Ex. No. | Ring B | Q | R¹ | Physical Properties |
|---|---|---|---|---|
| 11 | 2-CH₃O-phenyl | —S— | 2-pyrimidinyl | M.p. 107–108° C. |
| 12 | 2-CH₃O-phenyl | —S— | H | M.p. 165–166.5° C. |

Reference Example 13

(1) To a stirred mixture of tetrahydrofuran (400 ml) and ethylene glycol (60 ml) is added sodium hydride (60% dispersion-type, 3.38 g) under ice-cooling, and thereto is added 4,6-dichloro-5-(4-methyllphenyl)pyrimidine (20.0 g). The mixture is stirred under ice-cooling for 30 minutes, and stirred at room temperature for two hours. The mixture is made weak acidic with acetic acid, and concentrated under reduced pressure. The residue is dissolved in ethyl acetate, washed, dried, and concentrated to dryness under reduced pressure. The residue is crystallized from hexane to give 2-{6-chloro-5-(4-methylphenyl)pyrimidin-4-yloxy}ethanol (21.85 g).

M.p. 62°–64° C.

(2) A mixture of 2-{6-chloro-5-(4-methylphenyl)pyrimidin-4-yloxy}ethanol (21.85 g), sodium azide (10.7 g) and dimethyformamide (260 ml) is heated with stirring at 75°–80° C. overnight. After cooling, the mixture is treated with water, and extracted with ethyl acetate. The ethyl acetate layer is washed, dried, and evaporated to remove the solvent. The residue is crystallized from hexane to give 2-{6-azido-5-(4-methylphenyl)pyrimidin-4-yloxy}ethanol (19.6 g).

M.p. 83.5°–85° C.

MS (m/z): 271 (M⁺)

(3) A mixture of 2-{6-azido-5-(4-methylphenyl)pyrimidin-4-yloxy}ethanol (19.6 g), 10% palladium-carbon (50% moist) (4.0 g) and ethanol (240 ml) is subjected to catalytic hydrogenation at room temperature under hydrogen atmosphere (1 atm) for one hour. The catalyst is removed by filtration, and the filtrate is concentrated under reduced pressure. The residue is recrystallized from ethyl acetate/n-hexane to give 2-{6-amino-5-(4-methylphenyl)pyrimidin-4-yloxy}ethanol (15.9 g).

M.p. 104°–105° C.

Reference Example 14

(1) To a solution of 4,6-dichloro-5-(4-methylphenyl)pyrimidine (4.14 g) in ether (20 ml) is added 27% ammonia-ethanol solution (30 ml), and the reaction mixture is reacted at room temperature in a sealed tube for three days. The mixture is concentrated under reduced pressure, and the residue is purified by silica gel column chromatography (solvent; hexane/ethyl acetate=(10:1)~ethyl acetate) to give 6-chloro-5-(4-methylphenyl)pyrimidin-4-amine (1.89 g).

M.p. 168°–171° C.

(2) A mixture of 6-chloro-5-(4-methylphenyl)pyrimidin-4-amine (500 mg), ethylene glycol(10 ml) and sodium hydride (60% dispersion-type, 0.46 g) is reacted at 70° C. for two hours, and reacted at 90° C. for five hours. The mixture is treated with saturated aqueous ammonium chloride solution, and extracted with ethyl acetate. The ethyl acetate layer is washed, dried, and evaporated to remove the solvent. The residue is crystallized from hexane/ethyl acetate to give 2-{6-amino-5-(4-methylphenyl)pyrimidin-4-yloxy}ethanol (422 mg).

M.p. 91.5°–93.5° C.

Reference Example 15

To a solution of 2-{6-amino-5-(4-methylphenyl)pyrimidin-4-yloxy}ethanol (7.54 g) in tetrahydrofuran (150 ml) is added sodium hydride (60% dispersion-type, 1.47 g), and thereto is added 5-bromo-2-chloropyrimidine (7.73 g), and the mixture is stirred at room temperature overnight. To the reaction solution is added saturated aqueous ammonium chloride solution, and the mixture is evaporated to remove the solvent. The precipitated crystals are collected by filtration, washed and dried. The crude crystals are purified by silica gel column chromatography (solvent; chloroform/methanol=100:1~80:1), and recrystallized from tetrahydrofuran/diethyl ether to give 6-[2-(5-bromopyrimidin-2-yloxy)ethoxy]-5-(4-methylphenyl)pyrimidin-4-amine (11.27 g).

M.p. 178.5°–179.5° C.

IR (nujol, cm-1): 3400, 3300, 3130, 1640, 1580

MS (m/z): 401,403 (M⁺)

Reference Example 16

(1) To a solution of 4,6-dichloropyrimidine (1.33 g) and 4-tertbutylbenzenesulfonamide (1.96 g) in dimethylformamide (20 ml) is added sodium hydride (60% dispersion-type, 714 mg). The mixture is stirred at room temperature for two hours, and the reaction solution is diluted with 10% hydrochloric acid and water. The mixture is extracted with ethyl acetate, and the ethyl acetate layer is washed, dried, and evaporated to remove the solvent. The residue is recrystallized from ethyl acetate to give 4-tert-butyl-N-(6-chloropyrimidin-4-yl)benzenesulfonamide (2.02 g).

M.p. 225°–226.5° C.

IR (nujol, cm-1): 3035, 1630, 1595, 1575

MS (m/z): 325 (M⁺)

(2) To ethylene glycol (20 ml) is added sodium hydride (60% dispersion-type, 1.03 g), and thereto is added 4-tert-butyl-N-(6-chloropyrimidin-4-yl)benzenesulfonamide (1.66 g). The mixture is stirred at 60° C. for 20 hours. After cooling, the mixture is acidified with 10% hydrochloric acid, and extracted with ethyl acetate. The ethyl acetate layer is washed, dried, and evaporated to remove the solvent. The residue is crystallized from ethyl acetate to give 4-tertbutyl-N-{6-(2-hydroxyethoxy)pyrimidin-4-yl}benzenesulfonamide (1.58 g).

M.p. 169°–170.5° C.

IR (nujol, cm-1): 3440, 1600, 1570

FABMS (m/z): 352 (M$^+$)

(3) To a solution of 4-tert-butyl-N-[6-(2-hydroxyethoxy)pyrimidin-4-yl)benzenesulfonamide (210 mg) in dimethylformamide (4 ml) is added N-bromosuccinimide (116 mg), and the mixture is stirred at room temperature for one hour. The mixture is treated with aqueous sodium hydrogen sulfite solution, and extracted with ethyl acetate. The ethyl acetate layer is washed, dried and evaporated to remove the solvent. The residue is purified by silica gel column chromatography (solvent; chloroform/methanol=40:1), and recrystallized from hexane/ethyl acetate to give N-[5-bromo-6-(2-hydroxyethoxy)pyrimidin-4-yl]-4-tert-butylbenzenesulfonamide (169 mg).

M.p. 146°–147.5° C.

IR (nujol, cm-1): 3360, 3200, 1620, 1575

FABMS (m/z): 432,430 (MH$^+$)

(4) To a solution of N-[5-bromo-6-(2-hydroxyethoxy)pyrimidin-4-yl]-4-tert-butylbenzenesulfonamide (3.10 g) in dimethylacetamide (30 ml) is added sodium hydride (60% dispersion-type, 720 mg), and the mixture is stirred at room temperature for 30 minutes. To the mixture is added 2-chloro-5-methylthiopyrimidine (1.51 g), and the mixture is stirred at room temperature overnight. The reaction solution is treated with 10% hydrochloric acid and saturated ammonium chloride solution, and extracted with ethyl acetate. The ethyl acetate layer is washed, dried, and evaporated to remove the solvent. The residue is purified by silica gel column chromatography (solvent; chloroform/ethyl acetate=10:1), and recrystallized from hexane/ethyl acetate to give N-{5-bromo-6-[2-(5-methylthiopyrimidin-2-yloxy)ethoxy]pyrimidin-4-yl}-4-tert-butylbenzenesulfonamide (3.34 g).

M.p. 120°–121° C.

IR (nujol, cm-1): 1585, 1575, 1550

FABMS (m/z): 556,554 (MH$^+$)

Reference Example 17

(1) To a mixture of 4,6-dichloropyrimidine (5.0 g), ethylene glycol (100 ml) and tetrahydrofuran (100 ml) is added sodium hydride (60% dispersion-type, 1.34 g) under ice-cooling. The mixture is stirred at the same temperature for two hours, and evaporated to remove the solvent. The residue is extracted with ethyl acetate, and the ethyl acetate extract is dried, and concentrated under reduced pressure. The residue is purified by silica gel column chromatography (solvent; chloroform/ethyl acetate=5:1~2:1) to give 2-(6-chloropyrimidin-4-yloxy)ethanol (5.67 g) as an oily product.

IR (nujol, cm-1): 3300, 1575, 1545

FABMS (m/z): 175 (MH$^+$)

(2) To a solution of 2-(6-chloropyrimidin-4-yloxy)ethanol (5.61 g) in dimethylformamide (60 ml) is added sodium azide (4.18 g), and the mixture is stirred at 70° C. for 20 hours. After cooling, the reaction solution is treated with water, and extracted with ethyl acetate. The ethyl acetate layer is dried, and evaporated to remove the solvent. The residue is purified by silica gel column chromatography (solvent; hexane/ethyl acetate=1:1) to give 2-(6-azidopyrimidin-4-yloxy)ethanol (1.68 g).

M.p. 49°–50° C.

IR (nujol, cm-1): 3280, 2070, 1600, 1550

FABMS (m/z): 181 (MH$^+$)

(3) A mixture of 2-(6-azidopyrimidin-4-yloxy)ethanol (1.64 g), 10% palladium-carbon (0.25 g) and ethanol (20 ml) is subjected to catalytic hydrogenation at room temperature for one hour under hydrogen atmosphere (1 atm). The catalyst is removed by filtration, and the filtrate is concentrated. The residue is recrystallized from ethanol/diethyl ether to give 2-(6-aminopyrimidin-4-yloxy)ethanol (1.11 g).

M.p. 133°–137° C.

IR (nujol, cm-1): 3360, 3200, 1660, 1610, 1550

FABMS (m/z): 156 (MH$^+$)

(4) To a suspension of 2-(6-aminopyrimidin-4-yloxy)ethanol (400 mg) in methanol (4 ml) is added dropwise a solution of bromine (437 mg) in methanol (2 ml). The mixture is evaporated to remove the solvent, and the residue is dissolved in ethyl acetate. The mixture is treated with saturated aqueous sodium hydrogen carbonate solution, and extracted with ethyl acetate/tetrahydrofuran. The organic layer is washed, dried, and evaporated to remove the solvent to give 2-(6-amino-5-bromopyrimidin-4-yloxy)ethanol (632 mg).

IR (nujol, cm-1): 3480, 3420, 3390, 3290, 1640, 1580

MS (m/z): 235,233 (M$^+$)

(5) To a solution of 2-(6-amino-5-bromopyrimidin-4-yloxy)ethanol (611 mg) in dimethylformamide (20 ml) is added sodium hydride (60% dispersion-type, 125 mg), and the mixture is stirred for 20 minutes. To the mixture is added 2-chloro-5-methylthiopyrimidine (461 mg), and the mixture is stirred at room temperature for three hours. To the mixture is added ice-water, and the mixture is extracted with ethyl acetate. The ethyl acetate layer is washed, dried, and evaporated to remove the solvent. The residue is purified by silica gel column chromatography (solvent; chloroform/methanol=20:1), and crystallized from ethyl acetate/diisopropyl ether to give 5-bromo-6-[2-(5-methythiopyrimidin-2-yloxy)ethoxy]pyrimidine-4-amine (501 mg).

M.p. 126°–129° C.

IR (nujol, cm-1): 3450, 3270, 1635, 1585, 1570, 1540

MS (m/z): 359, 357 (M$^+$)

(6) To a solution of 5-bromo-6-[2-(5-methylthiopyrimidin-2-yloxy)ethoxy]pyrimidine-4-amine (102 mg) in tetrahydrofuran (2 ml) is added sodium hydride (60% dispersion-type, 34 mg), and thereto is added 4-tert-butylbenzenesulfonyl chloride (198 mg). The mixture is stirred at room temperature for 20 minutes, and thereto are added a drop of pyridine and water. The mixture is stirred at room temperature for 30 minutes, and neutralized with saturated aqueous ammonium chloride solution. The mixture is extracted with ethyl acetate, and the ethyl acetate layer is washed, dried, and evaporated to remove the solvent. The residue is purified by preparative thin layer chromatography (solvent; chloroform/methanol=15:1), and recrystallized from hexane/ethyl acetate to give N-{5-bromo-6-[2-(5-methylthiopyrimidin-2-yloxy)ethoxy]pyrimidin-4-yl}-4-tert-butylbenzenesulfonamide (135 mg). The physical properties thereof are the same as those of the compound obtained in Reference Example 16-(4).

Reference Example 18

(1) To a solution of diethyl (4-methylphenyl)malonate (9.45 g) and butyramidine hydrochloride (5.00 g) in methanol (25 ml) is added 28% sodium methoxide (19.67 g) under ice-cooling, and the mixture is stirred at room temperature overnight. After the reaction is complete, the reaction solution is concentrated to the half volume thereof, and the resultant is diluted with water. The mixture is acidified with 10% hydrochloric acid, and the precipitated crystals are collected by filtration, washed, and dried to give 5-(4-methylphenyl)-4,6-dihydroxy-2-n-propylpyrimidine (5.17 g) as crystalline powder.

M.p. >300° C.

(2) A mixture of the above product (5.14 g), diethylphenylamine (5 ml) and phosphorus oxychloride (20 ml) is refluxed for two hours. After the reaction is complete, the mixture is evaporated to remove phosphorus oxychloride, and poured gradually into water (300 ml). The mixture is stirred at room temperature for 20 minutes, and extracted with ether. The extract is washed, dried, treated with activated carbon, and evaporated to remove the solvent to give 5-(4-methylphenyl)-4,6-dichloro-2-n-propylpyrimidine (5.91 g) as crystals.

M.p. 91°–93° C.

(3) To a suspension of the above product (2.10 g) in dimethylsulfoxide (25 ml) are added 4-tert-butylbenzenesulfonamide (1.91 g) and potassium carbonate (4.13 g), and the mixture is stirred at 80° C. for 9 hours. After cooling, the reaction mixture is added into cold hydrochloride acid, and the mixture is extracted with ethyl acetate. The extract is washed, dried, and evaporated to remove the solvent. The residue is purified by silica gel column chromatography (solvent; chloroform/ethyl acetate=50:1), and crystallized from n-hexane to give 4-tert-butyl-N-[6-chloro-5-(4-methylphenyl)-2-n-propylpyrimidin-4-yl]benzenesulfonamide (3.0 g) as powder.

M.p. 138°–139° C.

(4) To a solution of the above product (2.94 g) in ethylene glycol (50 ml) is added sodium (0.74 g) in portions at room temperature, and the mixture is stirred at 135° C. for 18 hours. After cooling, the reaction mixture is diluted with diluted hydrochloric acid under cooling, and extracted with ethyl acetate. The extract is washed, dried, and evaporated to remove the solvent. The residue is purified by silica gel column chromatography (solvent; chloroform/ethyl acetate=50:1) to give 4-tert-butyl-N-[6-(2-hydroxyethoxy)-5-(4-methylphenyl)-2-n-propylpyrimidin-4-yl]benzensulfonamide (2.21 g) as crystalline powder.

M.p. 133°–134° C.

Reference Example 19

Diethyl (4-methylphenyl)malonate and isobutyramidine hydrochloride are treated in the same manner as in Reference Example 18 to give 4-tert-butyl-N-[6-(2-hydroxyethoxy)-5-(4-methylphenyl)-2-isopropylpyrimidin-4-yl]benzensulfonamide.

M.p. 143°–144° C.

Reference Example 20

(1) To a solution of thiophene (1.69 g) in anhydrous tetrahydrofuran (20 ml) is added dropwise a 1.6 M n-butyl lithium/n-hexane solution (11.4 ml) at 0° C. under argon atmosphere over a period of 30 minutes. To the mixture is added dropwise and gradually a solution of 5-(4-methylphenyl)-4,6-dichloropyrimidine (4.0 g) in anhydrous tetrahydrofuran (5 ml) at −60° C. The mixture is warmed to 0° C., and stirred for 1.5 hour. After the reaction is complete, to the mixture are added acetic acid (1.5 g) and water (0.25 g), and further added thereto a solution of 2,3-dichloro-5,6-dicyano-1,4-benzoquinone (5.70 g) in tetrahydrofuran (5 ml), and the mixture is stirred at 0° C. for one hour. The mixture is treated with an active charcoal, and extracted with a mixture of ethyl acetate and aqueous citric acid solution. The extract is washed, dried and evaporated to remove the solvent. The residue is purified by silica gel column chromatography (solvent; n-hexane/ethyl acetate=50:1) to give 5-(4-methylphenyl)-4,6-dichloro-2-(2-thienyl)pyrimidine (2.64 g) as powder.

M.p. 119.5°–120° C.

(2) The above product (2.64 g) is treated in the same manner as in Reference Example 18-(3) to give 4-tert-butyl-N-[6-chloro-5-(4-methylphenyl)-2-(2-thienyl)pyrimidin-4-yl]benzenesulfonamide (3.38 g) as powder.

M.p. >300° C.

(3) The above product (3.38 g) is treated in the same manner as in Reference Example 18-(4) to give 4-tert-butyl-N-[6-(2-hydroxyethoxy)-5-(4-methylphenyl)-2-(2-thienyl)pyrimidin-4-yl]benzenesulfonamide (2.11 g) as powder.

M.p. >300° C.

Reference Example 21

(1) A solution of 5-(4-methylphenyl)-4,6-dichloropyrimidine in ether is cooled at −30° C., and thereto is added dropwise a 1.8M phenyl lithium/cyclohexane solution. The reaction mixture is treated in the same manner as in Reference Example 20-(1) to give 5-(4-methylphenyl)-4,6-dichloro-2-phenylpyrimidine as crystalline powder.

M.p. 165°–166.5° C.

(2) The above product is treated in the same manner as in Reference Example 18-(3) to give 4-tert-butyl-N-[6-chloro-5-(4-methylphenyl)-2-phenylpyrimidin-4-yl]benzenesulfonamide as powder.

M.p. 249°–250° C.

(3) The above product is treated in the same manner in Reference Example 18-(4) to give 4-tert-butyl-N-[6-(2-hydroxyethoxy)-5-(4-methylphenyl)-2-phenylpyrimidin-4-yl]benzenesulfonamide as crystals.

M.p. 197.5°–198.5° C.

Reference Example 22

2-Chloro-5-bromopyrimidine and 2-furyltributyltin are treated in the same manner as in Example 190 to give 2-chloro-5-(2-furyl)pyrimidine.

M.p. 134.5°–136° C.

Reference Example 23

2-Chloro-5-bromopyrimidine and 2-thienyltributyltin are treated in the same manner as in Example 190 to give 2-chloro-5-(2-thienyl)pyridine.

M.p. 124.5°–125.5° C.

Reference Example 24

2-Chloro-5-bromopyrimidine and 3-thienyltributyltin are treated in the same manner as in Example 190 to give 2-chloro-5-(3-thienyl)pyrimidine.

M.p. 154°–157° C.

Reference Example 25

To a solution of 2-chloro-5-methoxypyrimidine (1.90 g) which is previously prepared by a method disclosed in J. Chem. Soc., 4590 (1960) in methylene chloride (30 ml) is added dropwise boron tribromide (4.97 ml) over a period of 15 minutes in a dry ice/acetone bath. The mixture is stirred at room temperature for 22 hours, and thereto is added dropwise methanol (30 ml) in a dry ice/acetone bath. The reaction mixture is concentrated under reduced pressure, and the pH value thereof is adjusted to pH 5 with aqueous sodium hydroxide solution. The mixture is extracted twice with ethyl acetate, and the extract is washed with water and brine, dried over anhydrous sodium sulfate, and evaporated to remove the solvent. The resulting crystals are washed with n-hexane to give 2-chloro-5-hydroxypyrimidine (1.47 g) as colorless crystals.

M.p. 194°–195° C.

Refeerence Example 26

(1) A solution of 3-hydroxymethylthiophene and thionyl chloride in methylene chloride is stirred under ice-cooling for 30 minutes. To the reaction mixture is added water, and the mixture is extracted with chloroform. The organic layer is washed with water, saturated aqueous sodium hydrogen carbonate solution and saturated brine, and dried. The residue is concentrated under reduced pressure to give 3-chloromethylthiophene (1.61 g).

(2) A mixture of 2-chloro-5-hydroxypyrimidine (200 mg), 3-chloromethylthiophene (610 mg), potassium carbonate (635 mg) and dimethylformamide (3 ml) is stirred at 50° C. for one hour. After the reaction is complete, to the reaction mixture is added water, and extracted with ethyl acetate. The organic layer is washed with water and saturated brine, dried, and concentrated under reduced pressure. The residue is purified by silica gel column chromatography (solvent; n-hexane/ethyl acetate=20:1→20:3), and evaporated to remove the solvent to give 2-chloro-5-(3-thienylmethoxy) pyrimidine (345 mg) as colorless needles.

M.p. 73°–76° C.

Reference Examples 27–32

The corresponding starting compounds are treated in the same manner as in Reference Example 26 to give the compounds as listed in Table 29.

TABLE 29

| Ref. Ex. No. | Structure | Physical Properties |
|---|---|---|
| 27 | Cl-pyrimidine-O—CH₂CH=CH₂ | Oil |
| 28 | Cl-pyrimidine-O—CH₂CN | M.p. 100–103° C. |
| 29 | Cl-pyrimidine-O—CH₂-cyclopropyl | M.p. 50–52° C. |
| 30 | Cl-pyrimidine-O—C₂H₅ | M.p. 65–67° C. |

TABLE 29-continued

| Ref. Ex. No. | Structure | Physical Properties |
|---|---|---|
| 31 | Cl-pyrimidine-O—CH(CH₃)₂ | M.p. 64–67° C. |
| 32 | Cl-pyrimidine-O—CH₂-pyridyl | M.p. 103–105° C. |

Effects of the Invention

The desired compounds [I] of the present invention and a pharmaceutically acceptable salt thereof show an excellent endothelin antagonistic activity so that they are useful in the prophylaxis or treatment of disorders associated with endothelin activities such as hypertension, pulmonary hypertension, renal hypertension, Raynaud disease, bronchial asthma, gastric ulcer, inflammatory bowel disease (Crohn's disease), shock, carcinogenesis, restenosis after angioplasty, organ dysfunction after transplantation, diabetes, thrombosis, arteriosclerosis, heart failure, acute renal insufficiency, glomerulonephritis, cyclosporin-induced nephrotoxicity, myocardial infarction, angina pectoris, arrhythmia, glaucoma, migraine, cerebrovascular spasm and cerebral infarction, and the like. Besides, the present compounds [I] and a pharmaceutically acceptable salt thereof are low toxic and hence, they show high safety as a medicament.

What is claimed is:

1. A benzenesulfonamide derivative of the formula [I]:

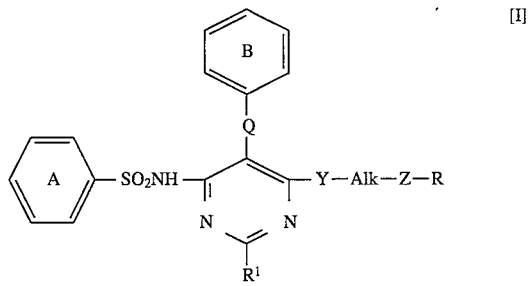

wherein Ring A is a benzene ring substituted by a lower alkyl group; one or two lower alkoxy groups; a lower alkoxycarbonyl-lower alkyl group; a hydroxy-substituted lower alkyl group; or a lower alkoxycarbonyl-lower alkoxy group, Ring B is a benzene ring substituted by formyl group; trifluoromethyl group; a lower alkyl group; one or two lower alkoxy groups; a lower alkylenedioxy group; a hydroxy-lower alkyl group; or a lower alkoxycarbonyl group, Q is a single bond or a group of the formula: —O— or —S—, Y is a group of the formula: —O—, Alk is a lower alkylene group, Z is a group of the formula: —O—, R is a phenyl group having optionally a substituent selected from amino group, nitro group, a halogen atom and a hydroxy-lower alkyl group; a pyridyl group having optionally a substituent selected from amino group, nitro group, trifluoromethyl group and a lower alkanoylamino group; a pyrimidinyl group having optionally a substituent selected from a halogen atom, formyl group, thienyl group, furyl group, pyridyl group, a lower alkyl group, a lower alkylthio group, a lower alkanoyl group, a lower alkynyl group, a lower alkenyloxy group, a lower alkoxy group, a lower alkylsulfinyl group, a lower alkylsulfonyl group, a cyano-substituted lower alkoxy group, thiazolyl group, a lower alkyl-substituted thienyl group, a lower alkyl-substituted pyrrolyl group, phenyl group and a lower alkoxyphenyl group; or benzothialolyl group, and $R^1$ is hydrogen atom, a lower alkyl group, pyridyl group, morpholinyl group or pyrimidiny group or a pharmaceutically acceptable salt thereof.

2. The compound according to claim 1, wherein Ring A is a benzene ring substituted by a lower alkyl group, Ring B is a benzene ring substituted by a halogen atom, a lower alkyl group or a lower alkoxy group, R is a pyrimidinyl group substituted by a halogen atom, thienyl group, furyl group or a lower alkylthio group, and $R^1$ is hydrogen atom or pyrimidinyl group.

3. 4-tert-Butyl-N-[5-(4-methylphenyl)-6-{2-(5-(3-thienyl)pyrimidin-2-yloxy)ethoxy}pyrimidin-4-yl]benzenesulfomamide, or a pharmaceutically acceptable salt thereof.

4. 4-tert-Butyl-N-[5-(4-methylphenyl)-6-{2-(5-methylthiopyrimidin-2-yloxy)ethoxy}pyrimidin-4-yl]benzenesulfomamide, or a pharmaceutically acceptable salt thereof.

5. 4-tert-Butyl-N-[5-(4-methylphenyl)-6-{2-(5-(2-furyl)pyrimidin-2-yloxy)ethoxy}pyrimidin-4-yl]benzenesulfomamide, or a pharmaceutically acceptable salt thereof.

6. 4-tert-Butyl-N-[5-(4-methylphenyl)-6-{2-(5-(2-thienyl)pyrimidin-2-yloxy)ethoxy}pyrimidin-4-yl]benzenesulfomamide, or a pharmaceutically acceptable salt thereof.

7. 4-tert-Butyl-N-[5-(4-methylphenyl)-6-{2-(5-bromopyrimidin-2-yloxy)ethoxy}pyrimidin-4-yl]benzenesulfomamide, or a pharmaceutically acceptable salt thereof.

8. 4-tert-Butyl-N-[5-(4-methylphenyl)-6-{2-(5-bromopyrimidin-2-yloxy)ethoxy}-2-(2-pyrimidyl)-pyrimidin-4-yl] benzenesulfomamide, or a pharmaceutically acceptable salt thereof.

9. 4-tert-Butyl-N-[5-(4-methylphenyl)-6-{2-(5-chloropyrimidin-2-yloxy)ethoxy}pyrimidin-4-yl]benzenesulfomamide, or a pharmaceutically acceptable salt thereof.

10. 4-tert-Butyl-N-[5-(4-methoxyphenyl)-6-{2-(5-methylthiopyrimidin-2-yloxy)ethoxy}pyrimidin-4-yl]benzenesulfomamide, or a pharmaceutically acceptable salt thereof.

11. 4-tert-Butyl-N-[5-(2-methoxyphenoxy)-6-{2-(5-(2-thienyl)pyrimidin-2-yloxy)ethoxy}pyrimidin-4-yl]benzenesulfomamide, or a pharmaceutically acceptable salt thereof.

12. 4-tert-Butyl-N-[5-(4-methylphenyl)-6-{2-(5-iodopyrimidin-2-yloxy)ethoxy}pyrimidin-4-yl]benzenesulfomamide, or a pharmaceutically acceptable salt thereof.

13. 4-tert-Butyl-N-[5-(4-chlorophenyl)-6-{2-(5-methylthiopyrimidin-2-yloxy)ethoxy}pyrimidin-4-yl]benzenesulfomamide, or a pharmaceutically acceptable salt thereof.

14. 4-tert-Butyl-N-[5-(2-methoxyphenylthio)-6-{2-(5-bromopyrimidin-2-yloxy)ethoxy}-2-(2-pyrimidyl)-pyrimidin-4-yl]benzenesulfomamide, or a pharmaceutically acceptable salt thereof.

15. 4-(1,1-Dimethyl-2-hydroxyethyl)-N-[5-(4-methylphenyl)-6-[2-(5-bromopyrimidin-2-yloxy)ethoxy]pyrimidin-4-yl]benzenesulfonamide or a pharmaceutically acceptable salt thereof.

* * * * *

UNITED STATES PATENT AND TRADEMARK OFFICE
CERTIFICATE OF CORRECTION

PATENT NO. : 5,589,478
DATED : December 31, 1996
INVENTOR(S) : Koichiro YAMADA et al.

It is certified that error appears in the above-indentified patent and that said Letters Patent is hereby corrected as shown below:

```
Claim 1, column 73, line 14, "benzothialolyl" should
read --benzothiazolyl--;
                    line 16, "pyrimidiny" should
read --pyrimidinyl--.

Claim 3, column 73, lines 26-27, "benzenesulfomamide"
should read --benzenesulfonamide--.

Claim 4, column 73, lines 29-30, "benzenesulfomamide"
should read --benzenesulfonamide--.

Claim 5, column 73, lines 32-33, "benzenesulfomamide"
should read --benzenesulfonamide--.

Claim 6, column 73, lines 35-36, "benzenesulfomamide"
should read --benzenesulfonamide--.
```

UNITED STATES PATENT AND TRADEMARK OFFICE
CERTIFICATE OF CORRECTION

PATENT NO. : 5,589,478
DATED : December 31, 1996
INVENTOR(S) : Koichiro YAMADA et al.

It is certified that error appears in the above-indentified patent and that said Letters Patent is hereby corrected as shown below:

Claim 7, column 74, lines 2-3, "benzenesulfomamide" should read --benzenesulfonamide--.

Claim 8, column 74, line 7, "benzenesulfomamide" should read --benzenesulfonamide--.

Claim 9, column 74, lines 10-11, "benzenesulfomamide" should read --benzenesulfonamide--.

Claim 10, column 74, lines 14-15, "benzenesulfomamide" should read --benzenesulfonamide--.

Claim 11, column 74, lines 18-19, "benzenesulfomamide" should read --benzenesulfonamide--.

UNITED STATES PATENT AND TRADEMARK OFFICE
CERTIFICATE OF CORRECTION

PATENT NO. : 5,589,478
DATED : December 31, 1996
INVENTOR(S) : Koichiro YAMADA et al.

It is certified that error appears in the above-indentified patent and that said Letters Patent is hereby corrected as shown below:

```
Claim 12, column 74, lines 21-22, "benzenesulfomamide"
should read --benzenesulfonamide--.

Claim 13, column 74, lines 24-25, "benzenesulfomamide"
should read --benzenesulfonamide--.

Claim 14, column 74, line 29, "benzenesulfomamide"
should read --benzenesulfonamide--.
```

Signed and Sealed this

Fourteenth Day of July, 1998

*Attest:*

BRUCE LEHMAN

*Attesting Officer*  *Commissioner of Patents and Trademarks*